(12) United States Patent
Jonckers et al.

(10) Patent No.: US 10,611,755 B2
(45) Date of Patent: Apr. 7, 2020

(54) ARYL SUBSTITUTED PYRIMIDINES FOR USE IN INFLUENZA VIRUS INFECTION

(71) Applicant: Janssen Sciences Ireland UC, Co Cork (IE)

(72) Inventors: Tim Hugo Maria Jonckers, Heist op den Berg (BE); David Craig McGowan, Brussels (BE); Jérôme Émile Georges Guillemont, Andé (FR); Werner Constant J Embrechts, Beerse (BE); Guillaume Jean Maurice Mercey, Montaure (FR); Christophe Francis Robert Nestor Buyck, Hamme (BE); Wendy Mia Albert Balemans, Kalmthout (BE); Pierre Jean-Marie Bernard Raboisson, Rosieres (FR)

(73) Assignee: Janssen Sciences Ireland UC, Little Island, Co Cork (IE)

( * ) Notice: Subject to any disclaimer, the term of this patent is extended or adjusted under 35 U.S.C. 154(b) by 0 days.

(21) Appl. No.: 16/071,649

(22) PCT Filed: Jan. 19, 2017

(86) PCT No.: PCT/EP2017/051105
§ 371 (c)(1),
(2) Date: Jul. 20, 2018

(87) PCT Pub. No.: WO2017/125506
PCT Pub. Date: Jul. 27, 2017

(65) Prior Publication Data
US 2019/0047989 A1 Feb. 14, 2019

(30) Foreign Application Priority Data

Jan. 20, 2016 (EP) .................................... 16152095

(51) Int. Cl.
*C07D 403/14* (2006.01)
*A61P 31/16* (2006.01)
*A61K 45/06* (2006.01)
*A61K 39/145* (2006.01)
*A61K 31/506* (2006.01)
*A61K 31/517* (2006.01)
*A61K 31/519* (2006.01)
*C07D 473/34* (2006.01)
*A61K 31/52* (2006.01)
*C07D 487/04* (2006.01)
*C07D 495/04* (2006.01)
*C07D 403/12* (2006.01)
*C07D 403/04* (2006.01)
*C07D 471/04* (2006.01)
*C07D 513/04* (2006.01)

(52) U.S. Cl.
CPC .......... *C07D 403/14* (2013.01); *A61K 31/506* (2013.01); *A61K 31/517* (2013.01); *A61K 31/519* (2013.01); *A61K 31/52* (2013.01); *A61K 39/145* (2013.01); *A61K 45/06* (2013.01); *A61P 31/16* (2018.01); *C07D 403/04* (2013.01); *C07D 403/12* (2013.01); *C07D 471/04* (2013.01); *C07D 473/34* (2013.01); *C07D 487/04* (2013.01); *C07D 495/04* (2013.01); *C07D 513/04* (2013.01)

(58) Field of Classification Search
CPC .. C07D 473/34; C07D 495/04; C07D 513/04; C07D 403/04; C07D 403/12; C07D 471/04; C07D 487/04; C07D 403/14; A61K 45/06; A61K 39/145; A61K 31/519; A61K 31/517; A61K 31/506; A61K 31/52; A61P 31/16
See application file for complete search history.

(56) References Cited

U.S. PATENT DOCUMENTS

| 8,937,080 B2* | 1/2015 | Raboisson | ........... | C07D 403/12 514/269 |
| 9,422,250 B2* | 8/2016 | McGowan | ........... | C07D 239/48 |
| 9,598,378 B2* | 3/2017 | McGowan | ........... | C07D 239/48 |

(Continued)

FOREIGN PATENT DOCUMENTS

| WO | 2007041130 A3 | 4/2007 |
| WO | 2010148197 A1 | 12/2010 |
| WO | 2012032065 A1 | 3/2012 |

(Continued)

OTHER PUBLICATIONS

International Search Report and Written Opinion for Corresponding Application No. PCT/EP2017/051105, dated Feb. 28, 2017.

(Continued)

*Primary Examiner* — Alexander R Pagano
*Assistant Examiner* — Ebenezer O Sackey

(57) ABSTRACT

The invention relates to compounds having the structure of formula (I) which can be used for the treatment of or against influenza infections.

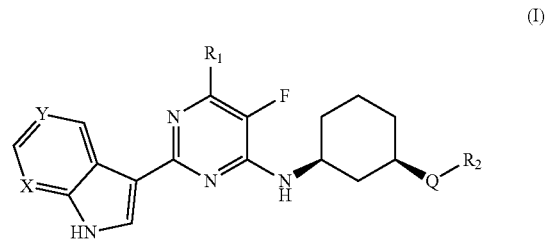

8 Claims, No Drawings

(56) References Cited

U.S. PATENT DOCUMENTS 9,617,289 B2 * 4/2017 Tahri .................. C07D 403/06
2018/0258074 A1 9/2018 Jonckers

FOREIGN PATENT DOCUMENTS

| WO | 2012083117 A1 | 6/2012 |
| WO | 2012083122 A1 | 6/2012 |
| WO | 2013019828 A1 | 2/2013 |
| WO | 2013184985 A1 | 12/2013 |

OTHER PUBLICATIONS

Chawla, et al., "Challenges in Polymorphism of Pharmaceuticals", Current Research & Information on Pharmaceutical Sciences, vol. 5(1): pp. 9-12 (Jan.-Mar. 2004).

Clark, et al, "Discovery of a Novel, First-in-Class, Orally Bioavailable Azaindole Inhibitor (VX-787) of Influenza PB2", Journal of Medicinal Chemistry, vol. 57 (15): pp. 6668-6678 (Jul. 14, 2014).

Narayanan, et al, "Developments in antivirals against influenza, smallpox and hemorrhagic fever viruses", Expert Opinion on Investigational Drugs, vol. 20(2); pp. 239-254 (Feb. 1, 2011).

Newman, et al., "Solid-State Analysis of the Active Pharmaceutical Ingredient in Drug Products", Drug Discovery Today, Oct. 19, 2003, pp. 898-905, vol. 8(19).

* cited by examiner

ARYL SUBSTITUTED PYRIMIDINES FOR USE IN INFLUENZA VIRUS INFECTION

CROSS-REFERENCE TO RELATED APPLICATIONS

This application is a national phase entry of International Application No. PCT/EP2017/051105, filed on Jan. 19, 2017, which claims priority to EP Patent Application No. 16152095.2, filed Jan. 20, 2016, each of which is incorporated herein in its entirety.

Influenza is a serious public health problem with a high incidence in the human population resulting in regular large-scale morbidity and mortality. It is a highly contagious airborne disease that causes an acute febrile illness. Systemic symptoms vary in severity from mild fatigue to respiratory failure and death. According to the WHO the average global burden of annual epidemics may be on the order of 1 billion cases, 3-5 million cases of severe illness and 300,000-500,000 deaths annually. Every year, influenza viruses circulate in humans, typically affecting 5-20% of the population in all age groups, with this figure rising up to 30% during major epidemics. Rates of serious illness and death are highest among persons aged >65 years, children aged <2 years, and persons of any age who have medical conditions that place them at increased risk for complications from influenza, such as chronic heart, lung, kidney, liver, blood or metabolic diseases, or weakened immune systems. Although deaths are infrequent among children, rates of hospitalization range from approximately 100 to 500 per 100,000 for children <5 years-old, depending on the presence or absence of co-morbid conditions. Hospitalization rates among children aged <24 months are comparable to rates reported among persons aged >65 years.

In the US, annual influenza epidemics lead to approximately 30 million outpatient visits, resulting in medical costs of $10 billion annually. Lost earnings due to illness and loss of life represent a cost of over $15 billion annually and the total US economic burden of annual influenza epidemics amounts to over $85 billion.

Pathogens that cause influenza are negative sense, single-stranded RNA viruses, which belong to the family of *Orthomyxoviridae*. There are three types of influenza viruses: A, B and C. Influenza A viruses are the most common form, which can spread in mammals and birds. The subtypes of influenza A are named by the types of surface proteins hemagglutinin (H) and neuraminidase (N). There are 18 different hemagglutinin and 11 known neuraminidases. Current seasonal influenza viruses found in human are mainly H1N1 and H3N2 subtypes. Influenza B viruses are usually found only in humans. They are not divided into subtypes, but can be further broken down into different strains. Circulating influenza viruses are highly variable each year, and both influenza A and B cause seasonal epidemics all over the world. Influenza C viruses give much milder symptoms, which do not cause epidemics.

All three types of viruses have similar genome structures. The genome comprises 8 segments, encoding 9-11 proteins, depending on the type. Influenza A encodes 11 proteins, which includes the surface proteins (hemagglutinin (HA) and neuraminidase (NA), the polymerase complex (PA, PB1 and PB2), nucleoprotein (NP), membrane proteins (M1 and M2), and other proteins (NS1, NS2, NEP). Among the three influenza virus types, influenza A has the highest rate of mutation. Influenza B evolves slower than A, but faster than C. The segmented genome allows gene exchanging between different viral strains, which generate new variants of influenza viruses.

Influenza virus can be transmitted among humans by direct contact with infected individuals or virus-contaminated material. One can also be infected by inhalation of suspended virus droplets in the air. Those droplets are generated by coughing, sneezing or talking of infected individuals. Seasonal influenza is characterized by a sudden onset of high fever, cough (usually dry), headache, muscle and joint pain, severe malaise (feeling unwell), sore throat and runny nose. Cough can be severe and can last two or more weeks. Most people recover from fever and other symptoms within a week without requiring medical attention. But influenza can cause severe illness or death especially in people at high risk as mentioned above. The time from infection to illness, known as the incubation period, is about two days.

The most effective way to prevent the disease and/or severe outcomes from the illness is vaccination. Safe and effective vaccines are available and have been used for more than 60 years. Among healthy adults, influenza vaccines can provide reasonable protection. However, vaccination comes with several limitations. First, influenza vaccine may be less effective in preventing illness among the elderly, and may only reduce severity of disease and incidence of complications and deaths. In addition, influenza vaccination is most effective when circulating viruses are well-matched with vaccine viruses, and the success of vaccination is largely dependent on the good prediction of the most prevalent virus type of the season. Rapid and continual evolution of influenza viral strains through antigenic drift, coupled with the short-lived nature of vaccine-induced immune responses to current influenza vaccines, means that vaccination with seasonally appropriate strains is required every year for prevention.

The current treatment of influenza uses either direct antiviral drugs, or medicines that release the influenza-induced symptoms. There are two classes of influenza antiviral drugs available on the market: neuraminidase inhibitors and M2 channel inhibitors. Neuraminidase inhibitors, oseltamivir or zanamivir, are the primary antiviral agents recommended for the prevention and treatment of influenza. These are effective against both influenza type A and B viruses. Development of resistance to these antiviral drugs has been identified during treatment of seasonal influenza and in sporadic oseltamivir-resistant 2009 H1N1 virus, but the public health impact has been limited to date. M2 channel inhibitors, such as amantadine and rimantadine (amantadanes), are active against influenza A strains, but not influenza B strains. Amantadane resistance among circulating influenza A viruses increased rapidly worldwide beginning during 2003-2004. Therefore, amantadine and rimantadine are not recommended for antiviral treatment or chemoprophylaxis of currently circulating influenza A virus strains.

In 2009, the novel swine H1N1 strain caused an unexpected influenza pandemic as a result of reassortment of genes from human, pig, and bird's H1N1 viruses. This past pandemic, together with the ongoing circulation of highly pathogenic avian H5N1 strains and the recent emergence of the H7N9 virus, a new reassortant of avian origin isolated in China, and associated with severe respiratory disease with 40% of mortality, which could potentially adapt for human-to-human transmission, highlighted the vulnerability of the world population to novel influenza strains. Although vaccination remains the main prophylactic strategy for controlling influenza infection, to bridge the period before a new vaccine becomes available and to treat the severe influenza cases, as well as to counter the problem of viral resistance, a wider choice of anti-influenza drugs is required. Development of new influenza antivirals has therefore again become a high priority and an unmet medical need.

The current invention relates to a compound of formula (I) which can be used for the treatment of, or against viral influenza infections:

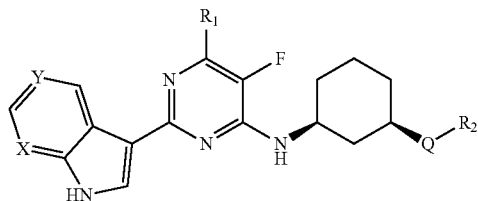

a stereo-isomeric form, a pharmaceutically acceptable salt, solvate or polymorph thereof, wherein
X is selected from —CF or N;
Y is selected from N, —CF, —C—Cl, —C—CN or —C—CH$_3$;
R$_1$ is selected from —H, —CH$_3$, —COOH, —CF$_3$, -cyclopropyl, —CONH$_2$, —CONH(C$_{1-3}$alkyl), or —CON(C$_{1-3}$alkyl)$_2$;
Q is selected from N or O and
R$_2$ is a heterocycle optionally substituted by halogen, cyano, C$_{1-3}$ alkyl, hydroxyl, amino, methoxy, —COOH, —CF$_3$ or cycloalkyl.

One of the preferred compounds according to the current invention has the following structure:

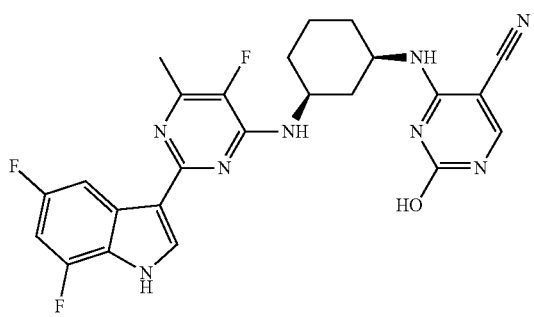 [SMILES: Cc1nc(-c2c[nH]c3c(F)cc(F)cc23)nc(N[C@H]2CCC[C@@H](Nc3nc(O)ncc3C#N)C2)c1F]

Part of the invention is also a pharmaceutical composition comprising a compound of formula (I) or a stereo-isomeric form, a pharmaceutically acceptable salt, solvate or polymorph thereof together with one or more pharmaceutically acceptable excipients, diluents or carriers.

The pharmaceutical composition may also include additional therapeutic agents, like another antiviral agent or an influenza vaccine, or both.

To the invention also belongs a compound of formula (I) or a stereo-isomeric form, a pharmaceutically acceptable salt, solvate or polymorph thereof, or a pharmaceutical composition for use as a medicament.

Additionally the invention relates to a compound of formula (I) or a stereo-isomeric form, a pharmaceutically acceptable salt, solvate or polymorph thereof or a pharmaceutical composition for use in the treatment of influenza.

Said use may also comprise the co-administration of an additional therapeutic agent, wherein said additional therapeutic agent is selected from an antiviral agent or influenza vaccine, or both.

Part of the invention is the use of a compound represented by the following structural formula (I)

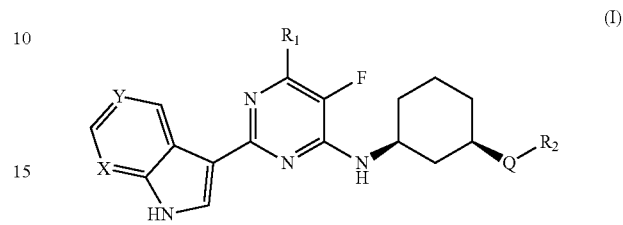

a stereo-isomeric form, a pharmaceutically acceptable salt, solvate or polymorph thereof, wherein
X is selected from —CF or N;
Y is selected from N, —CF, —C—Cl, —C—CN or —C—CH$_3$;
R$_1$ is selected from —H, —CH$_3$, —COOH, —CF$_3$, -cyclopropyl, —CONH$_2$, —CONH(C$_{1-3}$alkyl), or —CON(C$_{1-3}$alkyl)$_2$;
Q is selected from N or O and
R$_2$ is a heterocycle optionally substituted by halogen, cyano, C$_{1-3}$ alkyl, hydroxyl, amino, methoxy, —COOH, —CF$_3$ or cycloalkyl
for inhibiting the replication of influenza virus(es) in a biological sample or patient.

The term "alkyl" refers to a straight-chain or branched-chain saturated aliphatic hydrocarbon containing the specified number of carbon atoms.

The term "cycloalkyl" refers to a carbo-cyclic ring containing the specified number of carbon atoms.

The term "heterocycle" refers to molecules that are saturated or unsaturated comprising one or more heteroatoms selected from N, O or S, in particular from N and O. Said heterocycle may have 4, 5, 6 or 7 ring atoms and may be optionally fused to another ring system.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general, it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

The present compounds used in the current invention may also exist in their stereo-chemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereo-chemically isomeric forms, which said compounds might possess.

Said mixture may contain all diastereomers and/or enantiomers of the basic molecular structure of said compound. All stereo-chemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

EXAMPLES

Scheme 1.
Preparation of 3.

Scheme 1:

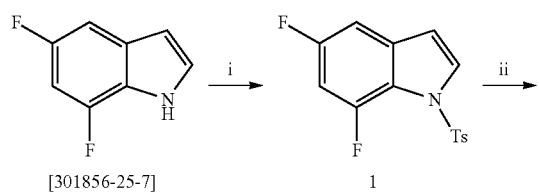

i) TBAHS, NaOH, Toluene ii) NBS, DMF iii) 4,4,4',4',5,5,5',5'-Octamethyl-2,2'-bi-1,3,2-dioxaborolane, Pd(dppf)Cl₂, KOAc, 1,4-dioxane, 90° C.

Scheme 2. General Scheme toward products of formula (I). Preparation of 10.

Scheme 2:

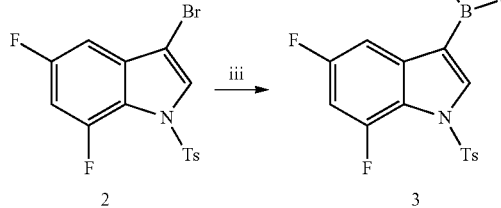

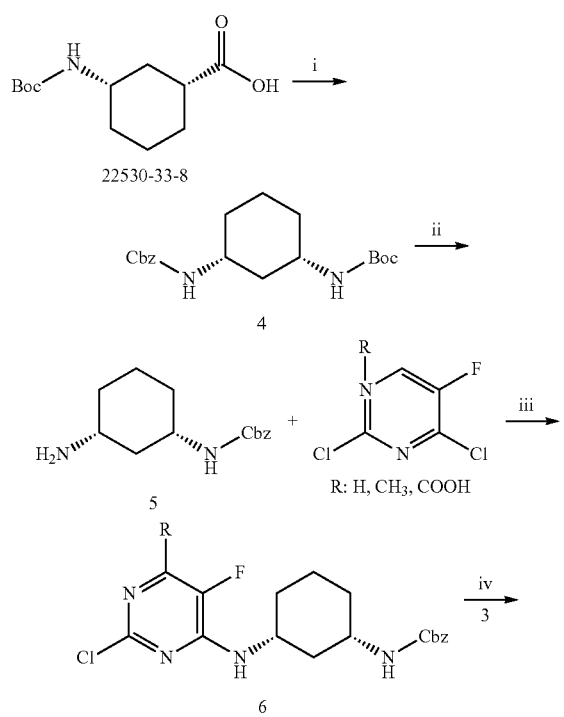

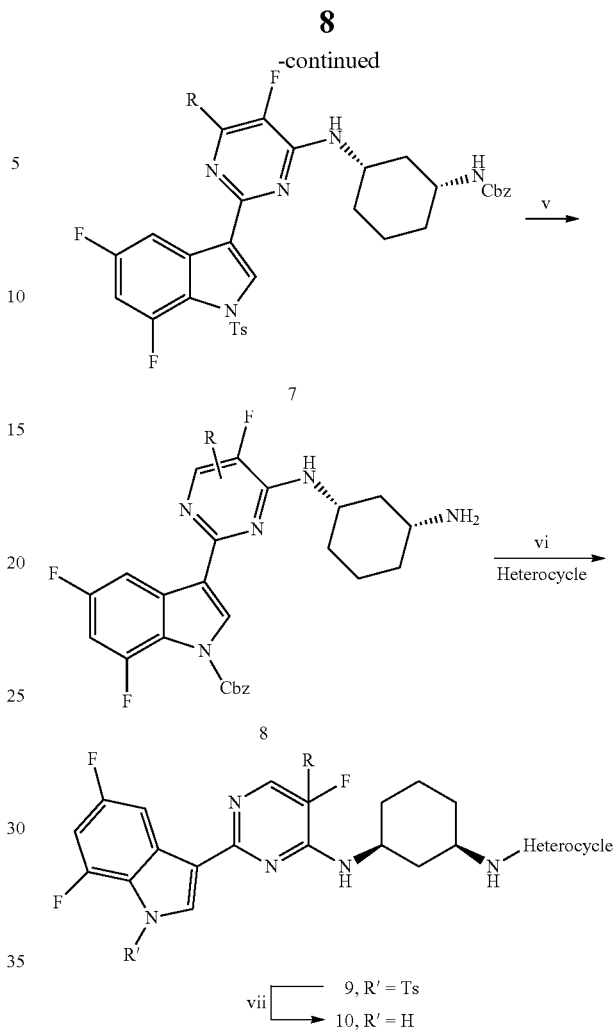

i) PhCH₂OH, DPPA, Et₃N, toluene, 100° C., 12 h ii) HCl, CH₂Cl₂, CH₃OH, rt, 48 h
iii) DIPEA, CH₃OH, THF, rt, 12 h iv) Na₂CO₃, Pd(PPh₃)₄, H₂O, 1,4-dioxane, 80° C., 12 h v) Pd/C, H₂, THF, vi) DIPEA, CH₃OH, THF, 80-90° C., 2 d vii) LiOH, 1,4-dioxane, H₂O, reflux Preparation of 1

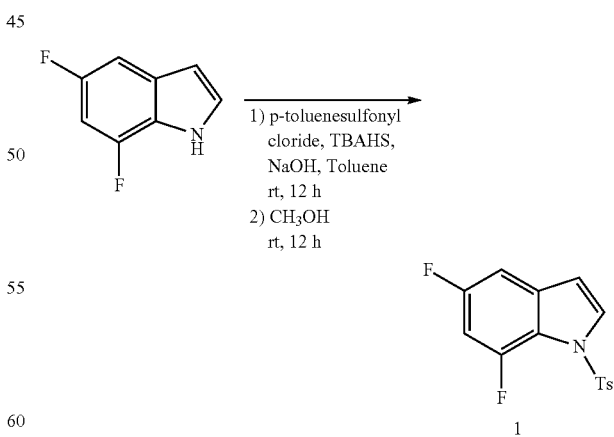

A solution of 5,7-difluoro-1H-indole (30 g, 195.91 mmol) in toluene (500 mL) was stirred under nitrogen. TBAHS (5 g, 14.7 mmol) was added, followed by NaOH (50% in H₂O) (105 mL), and the mixture was stirred vigorously. p-toluenesulfonyl chloride (63.5 g, 333 mmol) was added and the mixture was stirred for 12 h at rt. The resulting solution was diluted with 250 mL toluene and washed two times with water. The organic layer was dried over MgSO₄, the solids were removed by filtration, and the solvent of the filtrate was removed under reduced pressure. The crude was triturated in methanol and stirred for 12 h at rt. The precipitate was collected by filtration and dried in vacuo, yielding 5,7-difluoro-1-tosyl-1H-indole, 1.

Preparation of 2

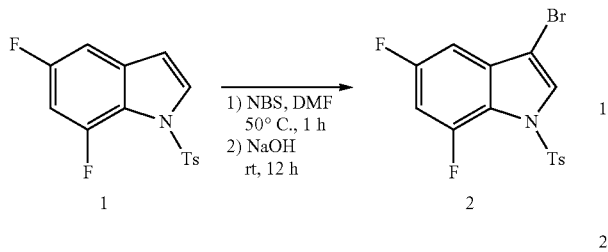

To a solution of 5,7-difluoro-1-tosyl-1H-indole, 1, (50.85 g, 165.46 mmol) in DMF (330 mL) was added NBS (35.34 g, 198.56 mmol) portion wise. Stirring was continued at 50° C. for one hour. The mixture was added drop wise to a stirred solution of NaOH (1N, 200 mL) in ice water (1 L) and stirred overnight. The precipitate was collected by filtration and dried in vacuo, yielding 3-bromo-5,7-difluoro-1-tosyl-1H-indole, 2.

Preparation of 3

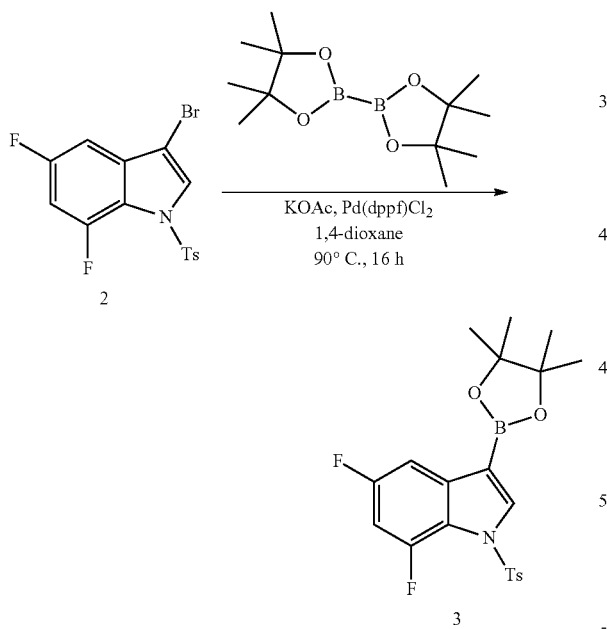

A mixture of 3-bromo-5,7-difluoro-1-tosyl-1H-indole, 2, (60 g, 155.35 mmol), 4,4,4',4',5,5,5',5'-octamethyl-2,2'-bi-1,3,2-dioxaborolane (118.35 g, 466.06 mmol), Pd(dppf)CL₂ (22.74 g, 31.07 mmol) and KOAc (45.74 g, 466.06 mmol) in 1,4-dioxane (1.5 L) was heated to 90° C. overnight under N₂. After filtration and concentration, the crude was purified via silica gel chromatography using a CH₂Cl₂ to heptane gradient. The fractions containing pure product were pooled, and the solvents were removed under reduced pressure yielding 5,7-difluoro-3-(4,4,5,5-tetramethyl-1,3,2-dioxaborolan-2-yl)-1-tosyl-1H-indole, 3.

Preparation of 4

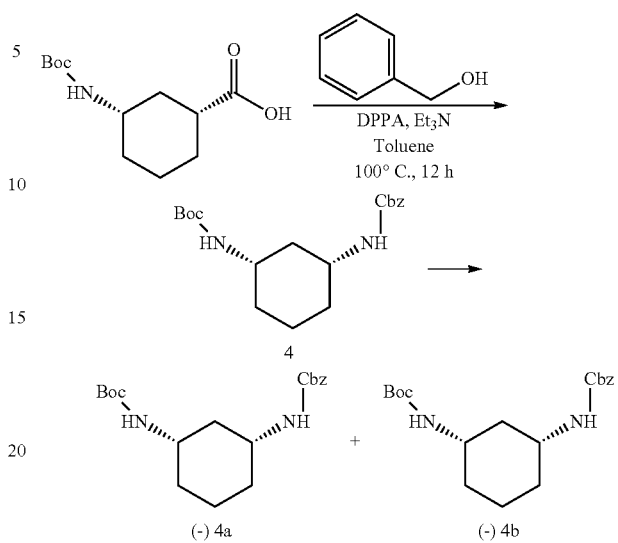

Triethylamine (35 mL, 251.6 mmol) and diphenylphosphoryl azide (39 mL, 181 mmol) were added to a stirred solution of cis-3-[(t-butoxycarbonyl)amino]cyclohexanecarboxylic acid (39 g, 160.25 mmol) in toluene (600 mL), and the resulting mixture was stirred at rt for 3 h. Benzyl alcohol (33.167 mL, 320.51 mmol) was added, and the mixture was heated to 100° C. After 12 h, the reaction mixture was cooled to rt, diluted with EtOAc, was washed with brine, dried (Na₂SO₄), the solids were removed by filtration and the filtrate concentrated in vacuo. A purification was performed via normal phase chiral separation (stationary phase: Daicel Chiralpak AD 2 kg, mobile phase: gradient from 80% heptane, 20% ethanol to 80% heptane, 20% ethanol) to afford (+)-benzyl t-butyl ((cis)-cyclohexane-1,3-diyl)dicarbamate, $[\alpha]_D^{20}$+10.9 (c 0.52, DMF) 4b and (−)-benzyl t-butyl ((cis)-cyclohexane-1,3-diyl)dicarbamate, $[\alpha]_D^{20}$−10.9 (c 0.47, DMF) 4a.

Preparation of 5

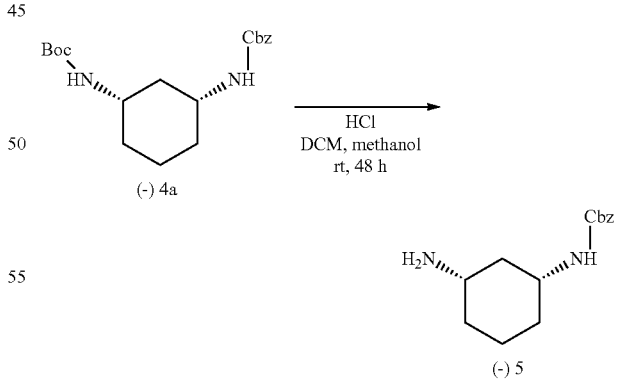

Into a 500 mL round bottom flask equipped with a magnetic stir bar, was added 4a (10 g, 28.7 mmol), CH₂Cl₂ (100 mL), and methanol (100 mL). 6M HCL in isopropanol was added slowly while stirring at room temperature for 48 hours. The solvent was removed under reduced pressure and the crude was stirred in diisopropylether containing isopropanol. The white precipitate was isolated by filtration and dried in vacuo yielding (−)5. $^1$H NMR (360 MHz, DMSO-$d_6$) δ ppm 1.01-1.13 (m, 1H) 1.16-1.36 (m, 3H) 1.66-1.80 (m, 2H) 1.86-1.99 (m, 1H) 2.14 (m, 1H) 2.95-3.17 (m, 1H) 3.28-3.51 (m, 1H) 4.95-5.08 (m, 2H) 7.27-7.45 (m, 5H) 8.21 (s, 3H). LC-MS ES$^+$ m/z=249.3; Rt: 1.48 min, method C Preparation of 6

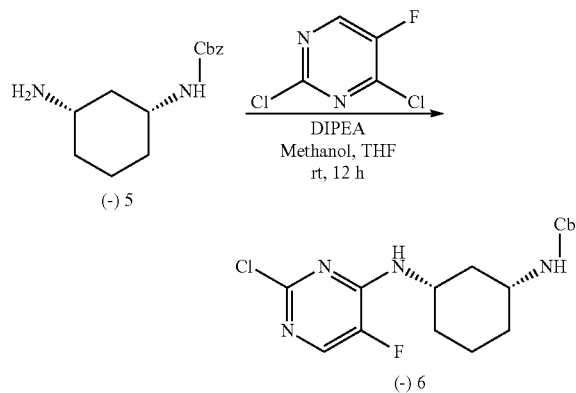

A solution of 5 (40 g, 140.46 mmol) and N,N-diisopropylethylamine (DIPEA, 72.61 mL, 421.37 mmol) was stirred at room temperature in CH$_3$OH (100 mL) and THF (400 mL). 2,4-Dichloro-5-fluoropyrimidine (23.5 g, 141 mmol) was added portion wise to the reaction mixture. The reaction mixture was allowed to stir for 18 h at room temperature. The solvent was evaporated, dissolved in ethyl acetate and washed with water and brine. The organic layer was dried over MgSO$_4$, the solids were removed by filtration, and the solvent of the filtrate was removed under reduced pressure. The residue was crystalized in diisopropylether with about 5% acetonitrile while stirring over weekend. The crystals were collected by filtration and dried in vacuo, yielding 6. $^1$H NMR (DMSO-$d_6$) δ: 7.99-8.14 (m, 2H), 7.24-7.45 (m, 6H), 5.01 (s, 2H), 3.82-3.99 (m, 1H), 1.99 (m, 1H), 1.67-1.85 (m, 3H), 1.17-1.44 (m, 3H), 1.00-1.15 (m, 1H). LC-MS ES$^+$ m/z=379.2; Rt: 1.94 min, method C.

Preparation of 7

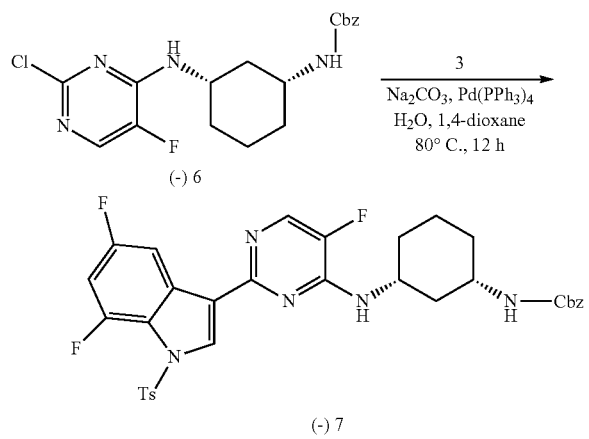

In a 250 mL round bottom flask equipped with a magnetic stir bar was placed a mixture of 3 (5 g, 11.54 mmol), 6 (3.64 g, 9.62 mmol) and Na$_2$CO$_3$ (1.70 g, 16.03 mmol) in H$_2$O (10 mL) and 1,4-dioxane (80 mL) was degassed with a stream of N$_2$ for 10 min. Pd(PPh$_3$)$_4$ (463 mg, 0.40 mmol) was added and the mixture was heated at 80° C. for 12 hours. The mixture was concentrated under reduced pressure and solved in CH$_2$Cl$_2$. The precipitate was removed by filtration and the filtrate was purified via silica gel column chromatography using a CH$_2$Cl$_2$ to CH$_2$Cl$_2$/CH$_3$OH gradient. The solvents of the best fractions were removed under reduced pressure to afford 7. LC-MS ES$^+$ m/z=650.2; Rt: 2.55 min, method C.

Preparation of 8

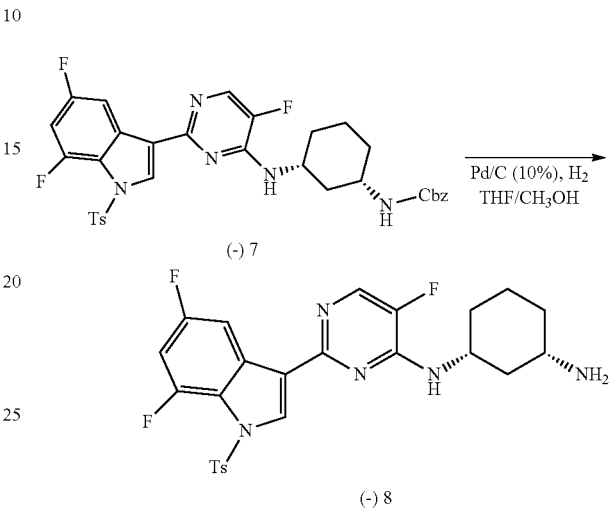

Pd/C (10%) (2.90 g, 2.71 mmol) was added to a mixture of CH$_3$OH (240 mL) and THF (240 mL) under N$_2$. Afterwards, (−)-7 (11.75 g, 18.09 mmol) was added and the reaction mixture was stirred at rt under H$_2$ until 1 eq. hydrogen was consumed. The catalyst was removed by filtration over Dicalite. The filtrate was concentrated under reduced pressure. The crude was dissolved in CH$_2$Cl$_2$ and treated with 6N HCl in isopropanol. The precipitate was dried in vacuo to afford 8. LC-MS ES$^+$ m/z=516.1; Rt: 2.10 min, method C.

Preparation of 9

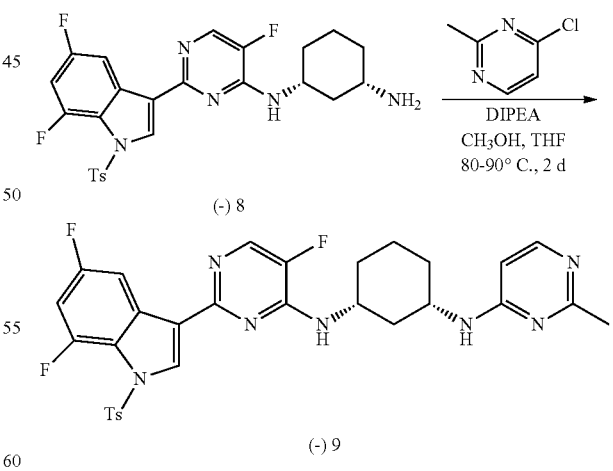

A solution of 8 (250 mg, 0.49 mmol) and DIPEA (0.25 mL, 1.46 mmol) in CH$_3$OH (1 mL) was stirred at room temperature. 4-chloro-2-methylpyrimidine (62 mg, 0.49 mmol) was added portion wise to the reaction mixture and stirred for 18 h at 80° C. An extra equivalent of 4-chloro-2-methylpyrimidine (62 mg, 0.49 mmol) was added and the entire mixture was heated at 90° C. for 24 h. The mixture was evaporated and crude 9 was used without further purification in the next step. LC-MS ES+ m/z=607.7; Rt: 2.38 min, method D.

Preparation of 10

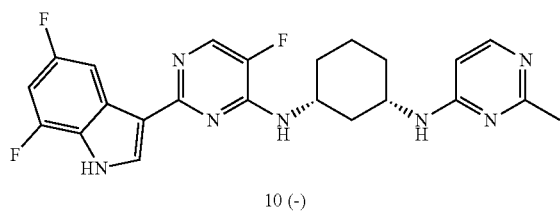 [SMILES: Cc1nccc(N[C@H]2CCC[C@@H](Nc3nc(-c4c[nH]c5c(F)cc(F)cc45)ncc3F)C2)n1]

10 (-)

In a 100 mL flask 9 (300 mg, 0.26 mmol) was stirred in 1,4-dioxane (9 mL) at 60° C., while a solution of LiOH (62 mg, 2.61 mmol) in water (1 mL) was added. The mixture was brought to reflux for 1 hour and was allowed to stir overnight at ambient temperature. The solvent was evaporated and the residue was taken in CH$_3$OH (30 mL), stirred and neutralized with HCl conc. The solution was purified by preparatory HPLC (Stationary phase: RP XBridge Prep C18 ODB-5 μm, 30×250 mm, Mobile phase: 0.25% NH$_4$HCO$_3$ solution in water, CH$_3$OH). The desired fractions were collected and evaporated to dryness. After addition of CH$_3$OH the solution was concentrated a second time to afford 10. $^1$H NMR (400 MHz, DMSO-d$_6$) δ ppm 1.14-1.42 (m, 3H) 1.48-1.59 (m, 1H) 1.80-1.92 (m, 1H) 1.94-2.09 (m, 2H) 2.24 (s, 3H) 2.26-2.31 (m, 1H) 4.05-4.30 (m, 2H) 6.22-6.30 (m, 1H) 7.02-7.08 (m, 1H) 7.20 (m, 1H) 7.50 (m, 1H) 7.88 (m, 1H) 8.04 (m, 1H) 8.12-8.17 (m, 2H) 12.17 (s, 1H). LC-MS ES+ m/z=453.8; Rt: 1.86 min, method D Preparation of 13

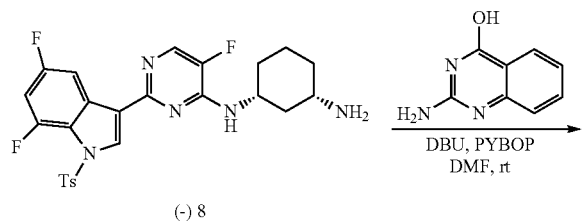

8 (65 mg, 0.40 mmol) was dispensed in 10 mL DMF, DBU (0.12 mL, 0.81 mmol) and PYBOP (252 mg, 0.49 mmol) were added. The mixture was stirred at rt until a homogeneous solution was obtained. 2-aminoquinazolin-4-ol (250 mg, 0.49 mmol) was added and the reaction mixture was stirred for 16 hours at rt. An extra equivalent of DBU, PYBOP and 2-aminoquinazolin-4-ol was added and the entire mixture was stirred over weekend at ambient temperature. The solvent was evaporated and the crude was purified by preparatory HPLC (Stationary phase: RP XBridge Prep C18 ODB-5 μm, 30×250 mm, Mobile phase: 0.25% NH$_4$HCO$_3$ solution in water, CH$_3$OH). The desired fractions were collected and evaporated to dryness. After addition of CH$_3$OH the solution was concentrated a second time to afford 13. LC-MS ES+ m/z=505.5; Rt: 1.80 min, method D Preparation of 17

17 was prepared according to the method to prepare 9. LC-MS ES+ m/z=627.9; Rt: 1.82 min, method C.

Preparation of 18

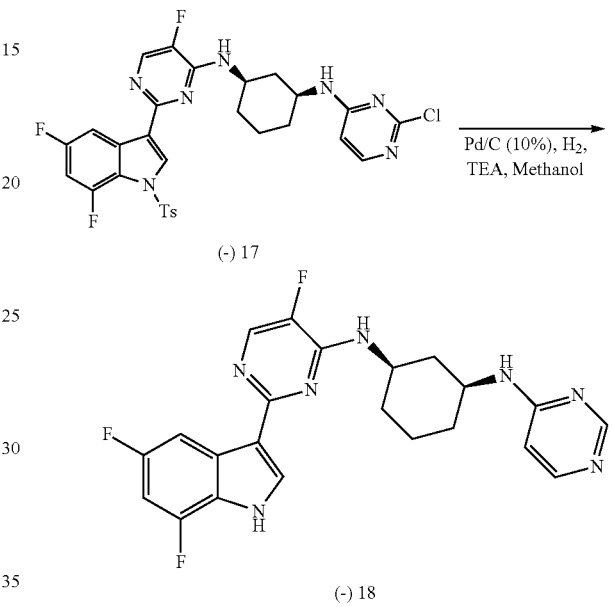

Pd/C (10%) (0.02 g, 0.18 mmol) was added to a mixture of CH$_3$OH (5 mL) under N$_2$. Afterwards, 17 (183 mg, 0.29 mmol) was added and the reaction mixture was stirred at rt under H$_2$ until 1 eq. H$_2$ was consumed. The catalyst was removed by filtration over Dicalite. The filtrate was concentrated under reduced pressure. The solvent was evaporated and the crude was purified by preparatory HPLC From 50% [25 mM NH$_4$HCO$_3$]-50% [MeCN: CH$_3$OH 1:1] to 25% [25 mM NH$_4$HCO$_3$]-75% [MeCN: CH$_3$OH 1:1]. The desired fractions were collected and evaporated to dryness. After addition of CH$_3$OH the solution was concentrated a second time to afford 18. $^1$H NMR (300 MHz, METHANOL-d$_4$) δ ppm 1.23-1.55 (m, 3H) 1.59-1.82 (m, 1H) 1.89-2.64 (m, 4H) 3.96-4.19 (m, 1H) 4.26-4.39 (m, 1H) 6.47 (br d, J=6.0 Hz, 1H) 6.76-6.86 (m, 1H) 7.89-8.00 (m, 2H) 8.04-8.11 (m, 2H) 8.31 (s, 1H). LC-MS ES+ m/z=440.1; Rt: 1.98 min, method C Preparation of 20

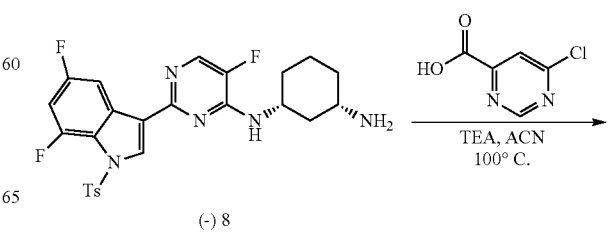

-continued

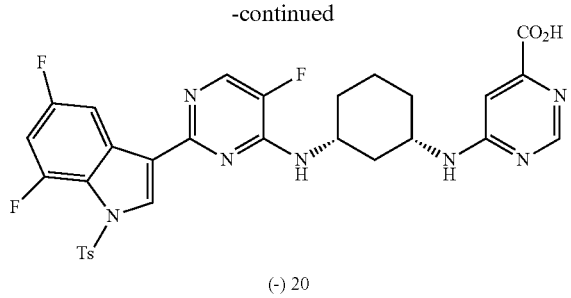

(-) 20

A mixture of 8 (76 mg, 0.21 mmol), 6-Chloropyrimidine-4-carboxylic acid (0.05 g, 0.31 mmol) and TEA (0.06 mL, 0.421 mmol) in ACN (2 mL) was stirred at 100° C. for 12 hours. The addition of 6-Chloropyrimidine-4-carboxylic acid (0.05 g, 0.315 mmol) was repeated three times over a period of 3 days and heated at 100° C. The solvent was evaporated and the crude was purified by reverse phase preparatory HPLC. The desired fractions were collected and evaporated to dryness to afford 20. $^1$H NMR (300 MHz, methanol-$d_4$) δ ppm 1.24-1.73 (m, 4H) 1.90-2.52 (m, 4H) 3.97-4.21 (m, 1H) 4.23-4.45 (m, 1H) 6.66-6.93 (m, 1H) 7.04 (s, 1H) 7.99 (d, J=4.1 Hz, 1H) 8.04 (br d, J=12.1 Hz, 1H) 8.08 (s, 1H) 8.21 (s, 1H). LC-MS ES$^+$ m/z=483.9; Rt: 2.10 min, method C Preparation of 21

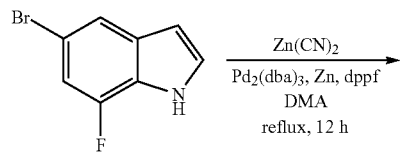

21

A mixture of 5-bromo-7-fluoro-1H-indole (4 g, 18.68 mmol), zinc cyanide (1.31 g, 11.21 mmol), Pd$_2$(dba)$_3$ (0.86 g, 0.93 mmol), Zn (0.31 g, 4.67 mmol) and dppf (1.04 g, 1.87 mmol) was dissolved in DMA (60 mL) and refluxed for 12 hours under N$_2$. The mixture was cooled to room temperature, filtered and the filtrate was concentrated in vacuo. The crude was extracted with EtOAc and the combined organic layers were washed with brine, dried over MgSO$_4$, the solids were removed by filtration, and the solvent of the filtrate was removed under reduced pressure. The crude was purified by silica column chromatography using a n-heptane to ethyl acetate gradient. The desired fractions were collected and concentrated under reduced pressure to afford 21. LC-MS ES$^+$ m/z=161.0; Rt: 0.579 min, method C.

Preparation of 22

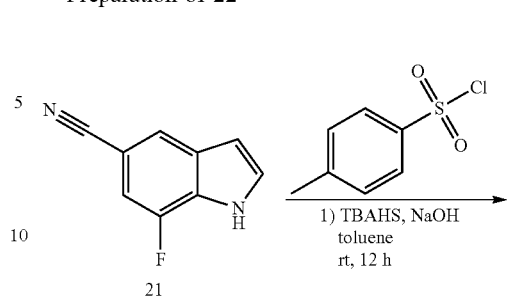

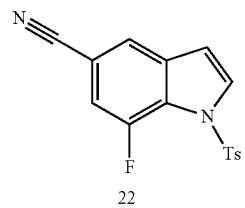

22

21 (1.9 g, 11.86 mmol) was added to toluene (30 mL) while stirring under nitrogen flow. Then, TBAHS (402 mg, 1.19 mmol) was added followed by NaOH (10% in H$_2$O) (10 mL) and the mixture was stirred vigorously. A solution of p-toluenesulfonyl chloride (3.39 g, 17.80 mmol) in toluene (30 mL) was added and the entire mixture was stirred at room temperature for 12 h. The solvent was removed under reduced pressure, and ethyl acetate was added. The organic layer was washed with water, dried over MgSO$_4$, the solids were removed by filtration, and the solvent of the filtrate was removed under reduced pressure. The resulting crude was purified via silica gel chromatography using a n-heptane to EtOAc gradient. The fractions containing pure product were pooled, and the solvents were removed under reduced pressure yielding 22. LC-MS ES$^+$ m/z=315.0; Rt: 1.01 min, method C.

Preparation of 23

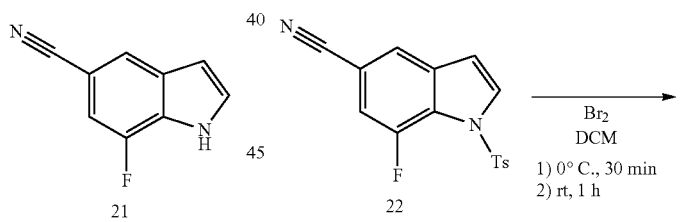

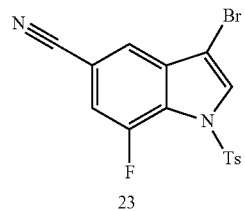

23

To a solution of 22 (1.7 mg, 5.41 mmol) in CH$_2$Cl$_2$ (15 mL) was added bromine (0.33 mL, 6.49 mmol) drop wise at 0° C. The mixture was stirred at 0° C. for 30 minutes and then stirred at room temperature for one additional hour. The reaction mixture was treated with a saturated solution of aqueous NaHCO$_3$. The organic layer was separated and washed with aq. Na$_2$S$_2$O$_3$, water, and brine, dried over MgSO$_4$, the solids were removed by filtration, and the solvent of the filtrate was removed under reduced pressure, yielding 23, used without further purification in the next step. LC-MS ES$^+$ m/z=394.0; Rt: 1.15 min, method C.

Preparation of 24

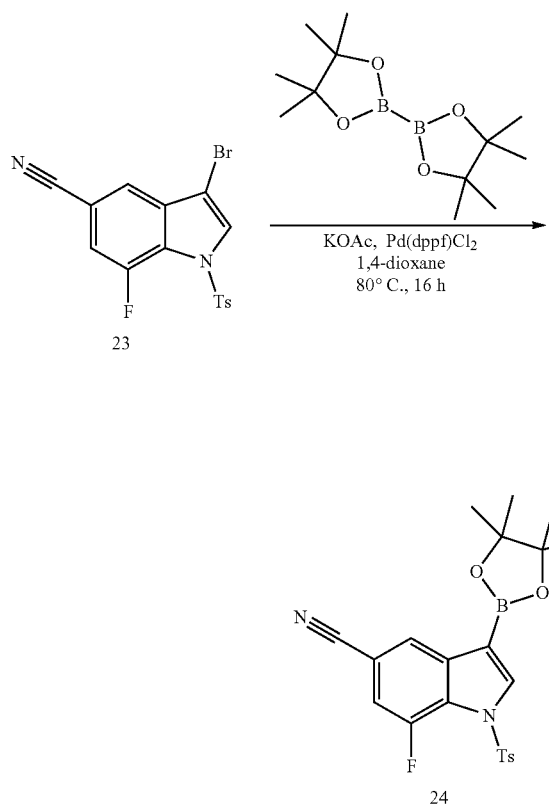

The solvent 1,4-dioxane (10 mL) was degassed for ten minutes. 23 (1.10 g, 2.80 mmol), bis(pinacolato)diboron (2.13 g, 8.39 mmol), Pd(dppf)Cl$_2$ (204 mg, 0.28 mmol) and KOAc (1.24 g, 12.59 mmol) were added at rt under inert atmosphere. The mixture was heated at 80° C. and stirred for 16 h. The resulting mixture was cooled to room temperature, filtered through a pad of celite and washed with EtOAc. After filtration and concentration, the crude was purified via silica gel chromatography using a n-heptane to EtOAc gradient. The fractions containing pure product were pooled, and the solvents were removed under reduced pressure yielding 24.

Preparation of 25

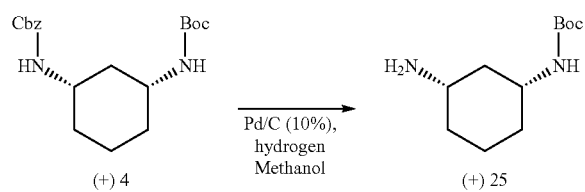 [SMILES: CC(C)(C)OC(=O)N[C@@H]1CCC[C@H](NC(=O)OCc2ccccc2)C1 ; CC(C)(C)OC(=O)N[C@@H]1CCC[C@H](N)C1]

Pd/C (10%) (3.05 g, 2.87 mmol) was added to CH$_3$OH (350 mL) under nitrogen gas. 4 (10 g, 28.70 mmol) was added. The reaction mixture was stirred at rt under H$_2$ until 1 eq. H$_2$ was absorbed. The catalyst was removed by filtration over dicalite under N$_2$ flow. The filtrate was concentrated under reduced pressure to afford 25, which was further used without purification.

Preparation of 26

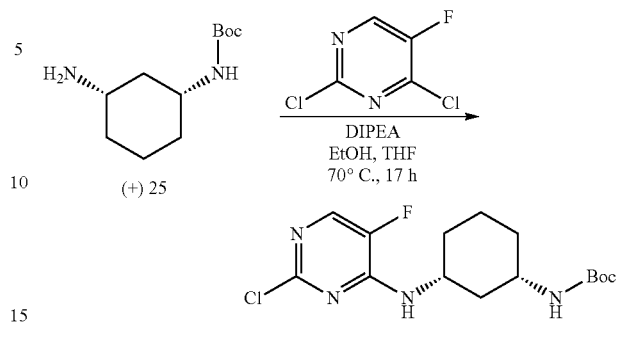

A mixture of 25 (6.15 g, 28.70 mmol), 2,4-dichloro-5-fluoro-pyrimidine (4.79 g, 28.70 mmol), DIPEA (29.7 mL, 172.2 mmol) in EtOH (130 mL) and THF (130 mL) was stirred and heated at 70° C. for 17 hours. The solvent of the reaction mixture was evaporated under reduced pressure. The resulting residue was taken up in water, extracted twice with EtOAc. The combined organic layers were washed with water, dried over MgSO$_4$, the solids were removed by filtration, and the solvent of the filtrate was removed under reduced pressure. The resulting crude was purified via silica gel chromatography using a CH$_2$Cl$_2$ to CH$_2$Cl$_2$/CH$_3$OH gradient. The fractions containing pure product were pooled, and the solvents were removed under reduced pressure yielding 26. LC-MS ES$^+$ m/z=345.0; Rt: 1.97 min, method C.

Preparation of 27

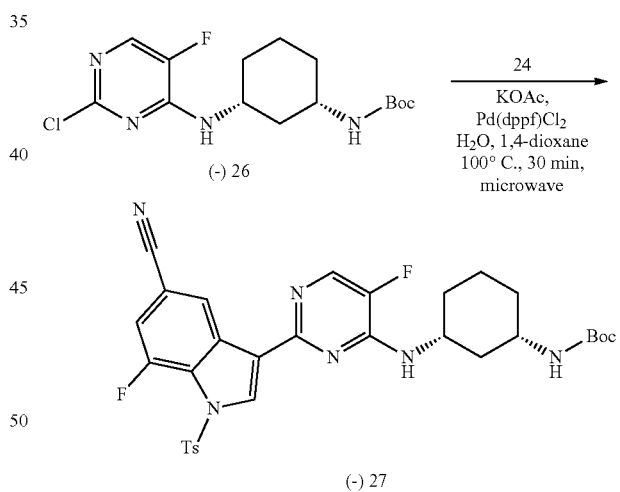

A mixture of 24 (1.10 g, 2.50 mmol), 26 (0.86 g, 2.50 mmol), Pd(dppf)Cl$_2$ (162 mg, 0.25 mmol), and KOAc (1.59 g, 7.50 mmol) in 1,4-dioxane (3 mL) and H$_2$O (0.3 mL) was degassed with N$_2$ and was heated to 100° C. for 30 minutes under microwave irradiation. The reaction mixture was filtered over celite and concentrated. Then, the mixture was dissolved in CH$_2$Cl$_2$ and washed with water. The organic layer was dried over MgSO$_4$, the solids were removed by filtration, and the solvent of the filtrate was removed under reduced pressure. The crude was purified via silica gel chromatography using a n-Heptane to EtOAc gradient. The fractions containing pure product were pooled, and the solvents were removed under reduced pressure, yielding 27. LC-MS ES$^+$ m/z=623; Rt: 1.34 min, method C.

Preparation of 28

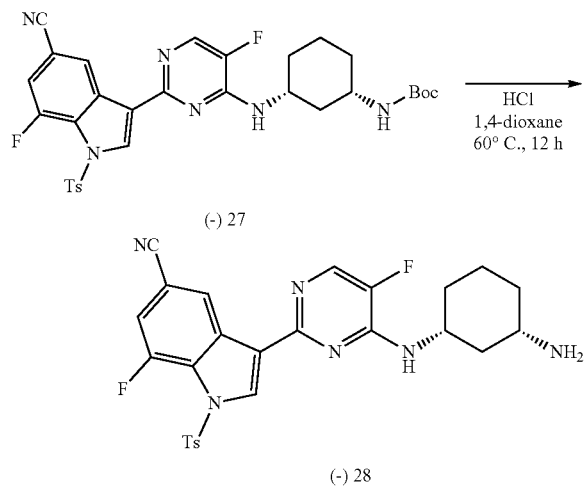

27 (400 mg, 0.64 mmol) was dissolved in 1,4-dioxane (2.5 mL), and then 4M HCl in 1,4-dioxane (2.41 mL, 9.64 mmol) was added slowly. The resulting mixture was stirred at 60° C. overnight. Then, the reaction mixture was evaporated to dryness, quenched by addition of a aqueous saturated NaHCO$_3$ solution, and extracted with CH$_2$Cl$_2$. The organic layer was dried over MgSO$_4$, the solids were removed by filtration, and the solvent of the filtrate was removed under reduced pressure to afford 28, which was used without purification in the next step. LC-MS ES$^+$ m/z=523; Rt: 0.89 min, method C.

Preparation of 29

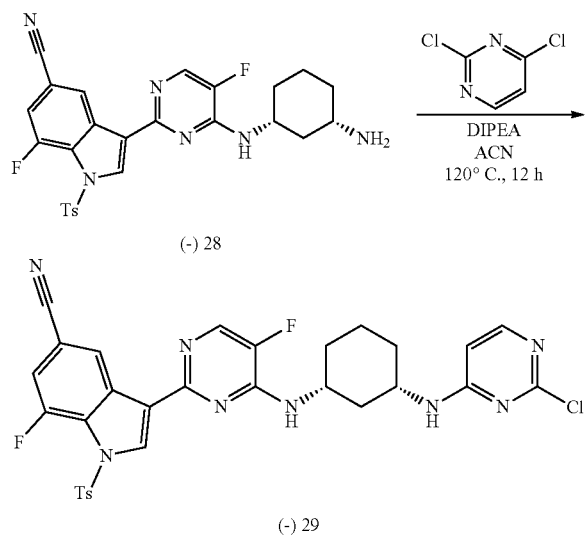

A mixture of 28 (0.2 g, 0.38 mmol), 2,4-dichloropyrimidine (0.10 g, 0.70 mmol) and DIPEA (0.2 mL, 1.15 mmol) in ACN (5 mL) was stirred at 120° C. for 12 hours. The solvent of the reaction mixture was removed under reduced pressure, and the crude was extracted with CH$_2$Cl$_2$ and washed with H$_2$O. The organic layer was dried over MgSO$_4$, the solids were removed by filtration, and the solvent of the filtrate was removed under reduced pressure to afford 29, which was used in the next step without further purification. LC-MS ES$^+$ m/z=634.9; Rt: 1.78 min, method C.

Preparation of 30

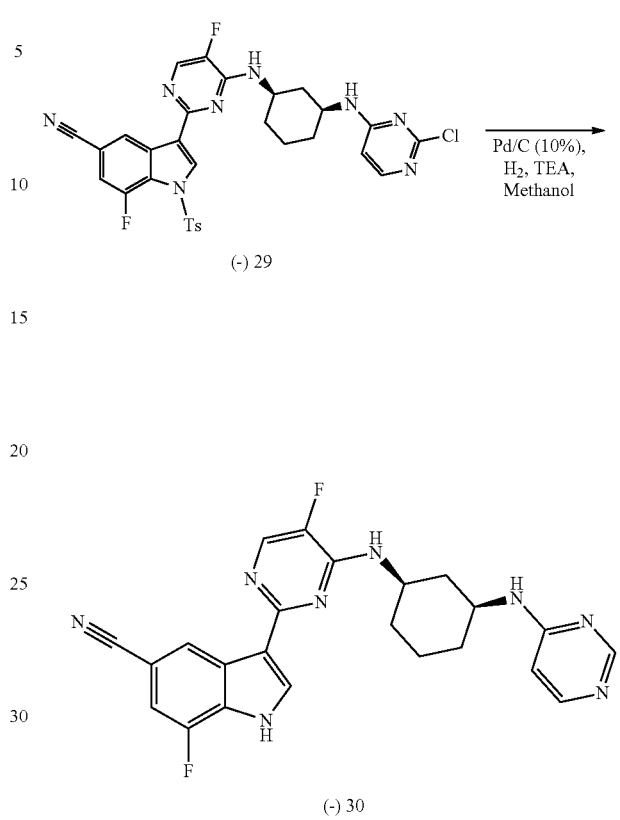

30 was prepared according to the methods to prepare 19. $^1$H NMR (300 MHz, methanol-d$_4$) δ ppm 1.29-1.49 (m, 3H) 1.66-1.84 (m, 1H) 1.93-2.16 (m, 2H) 2.19-2.30 (m, 1H) 2.49-2.61 (m, 1H) 3.96-4.18 (m, 1H) 4.19-4.37 (m, 1H) 6.42-6.53 (m, 1H) 7.24-7.32 (m, 1H) 7.87-7.95 (m, 1H) 7.97-8.03 (m, 1H) 8.15-8.24 (m, 2H) 8.82 (s, 1H). LC-MS ES$^+$ m/z=446.7; Rt: 2.05 min, method C.

Preparation of 31

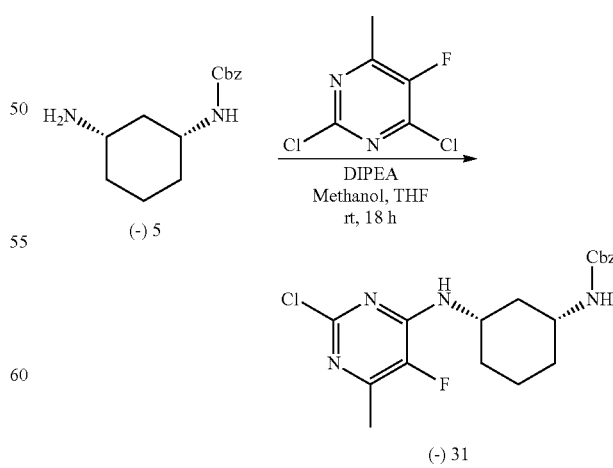

31 was prepared according to the method to prepare 6. LC-MS ES$^+$ m/z=393.2; Rt: 2.02 min, method C.

Preparation of 32

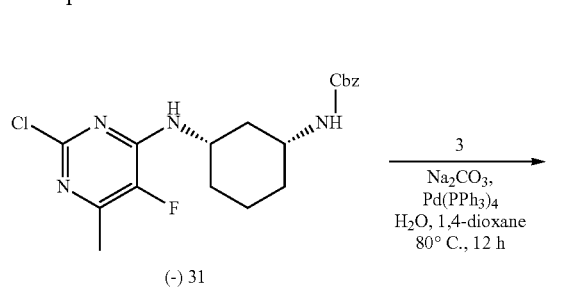

(-) 31

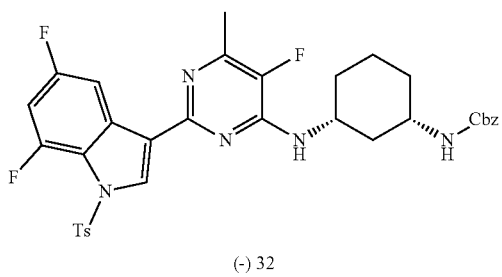

(-) 32

32 was prepared according to the method to prepare 7. LC-MS ES+ m/z=664.3; Rt: 1.05 min, method A.

Preparation of 33

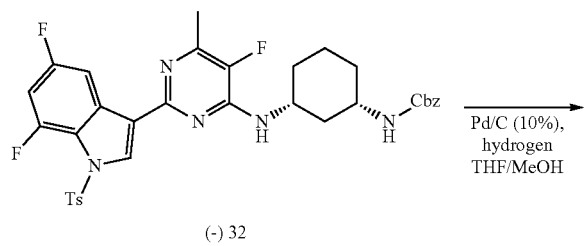

(-) 32

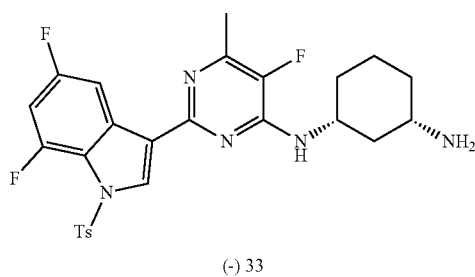

(-) 33

33 was prepared according to the method to prepare 8. LC-MS ES+ m/z=496.2; Rt: 0.89 min, method A.

Preparation of 34

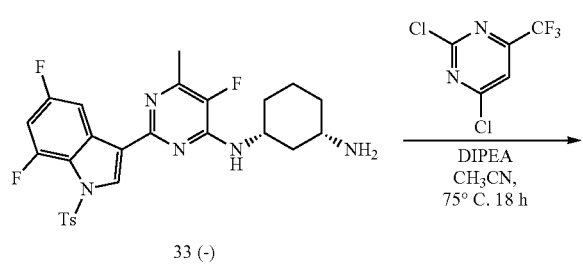

33 (-)

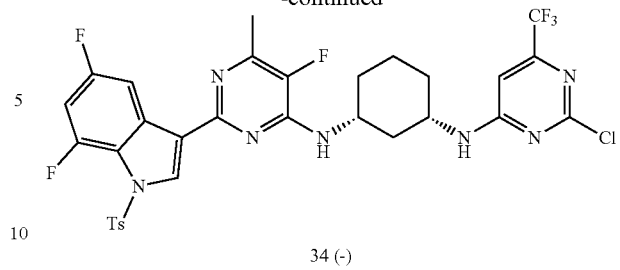

34 (-)

Into a 20 mL test tube equipped with a magnetic stir bar and sparged with nitrogen was placed 33 (350 mg, 0.66 mmol), ACN (7 mL), DIPEA (0.29 mL, 1.65 mmol) and 2,4-dichloro-6-(trifluoromethyl)pyrimidine (150.6 mg, 0.70 mmol). The flask was sealed and the mixture was allowed to stir at 75° C. for 18 h. The crude solution containing 34 was used without further purification in the next step. LC-MS ES+ m/z=710.3; Rt: 2.65 min, method C.

Preparation of 35

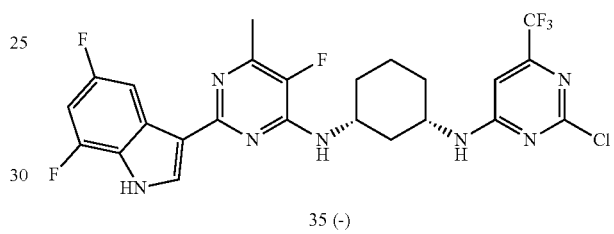

35 (-)

To the crude reaction mixture containing 34 was added 1,4-dioxane (8 mL), water (1 mL) and LiOH (10 eq.). The mixture was heated to 60° C. and stirred for 2 days. The solution was neutralized with conc. HCl before the solvent was removed under reduced pressure. The crude was purified via preparatory HPLC (stationary phase: RP XBridge Prep C18 ODB 5 μm, 30×250 mm, mobile phase: 0.25% NH4HCO3 solution in water, CH3OH). The desired fractions were collected and evaporated to dryness. After addition of CH3OH the solution was concentrated a second time to afford 35. LC-MS ES+ m/z=556.2; Rt: 2.31 min, method C.

Preparation of 43

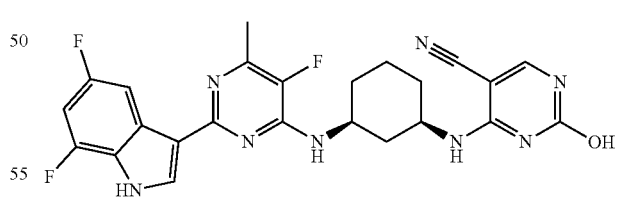

43

Into a 20 mL test tube equipped with a magnetic stir bar and sparged with nitrogen was placed (−)33 (0.3 g, 0.465 mmol), ACN (5 mL), DIPEA (0.24 mL, 1.39 mmol) and 2,4-dichloro-5-cyanopyrimidine (162 mg, 0.93 mmol). The flask was sealed and the mixture was allowed to stir at 70° C. for 18 h. The solvent was removed under reduced pressure and the crude was purified by silica gel chromatography (mobile phase gradient from heptane/AcOEt 75/25 to 50/50) to afford 240 mg of a white solid, 2-chloro-4-(((cis)-3-((2-(5,7-difluoro-1-tosyl-1H-indol-3-yl)-5-fluoro- 6-methylpyrimidin-4-yl)amino)cyclohexyl)amino)pyrimidine-5-carbonitrile. To this white solid was added water (0.54 mL), LiOH (0.72 g, 3.0 mmol), and THF (1.6 mL). The mixture was stirred at 60° C. for 72 h. Ethyl acetate was added and the mixture was washed with brine, dried over MgSO$_4$, the solids were removed by filtration and the solvent of the filtrate was removed under reduced pressure. The crude product was purified via silica gel chromatography (mobile phase gradient from CH$_2$Cl$_2$/CH$_3$OH 98/2 to 94/6). The pure fractions were pooled and the solvent removed under reduced pressure. The resulting white solid was triturated in ether then isolated by filtration to afford a white solid, 43. $[\alpha]_D^{20}$ −219.2 (c 0.25, DMF).

Preparation of 48

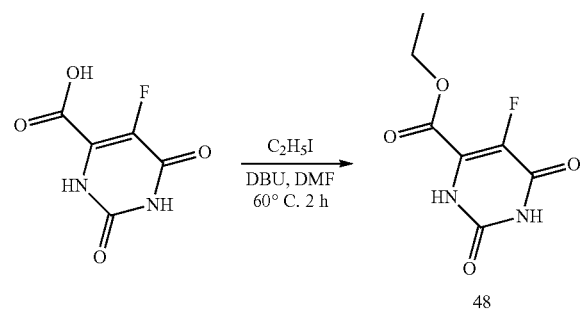

DBU (2.58 mL, 17.2 mmol) was added to a solution of 5-fluoroorotic acid (3 g, 17.2 mmol) in DMF (10 mL) After stirring for 30 minutes, iodoethane (2.69 mg, 17.2 mmol) was added to the solution and the mixture was heated to 60° C. for 2 hours. Water (100 mL) was added to the mixture, and the resulting precipitate was collected by filtration, washed with water, and dried to give 48 ethyl 5-fluoroorotate. LC-MS ES$^-$ m/z=200.9; Rt: 0.91 min, method D.

Preparation of 49

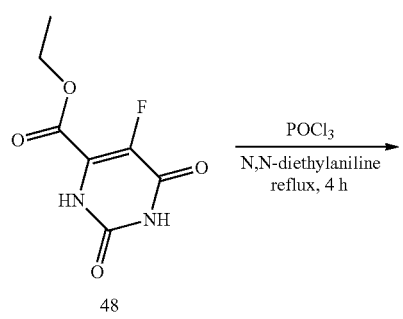

Ethyl 5-fluoroorotate 48 (2.13 g, 10.54 mmol) was added to a mixture of N,N-diethylaniline (1.09 mL, 7.16 mmol) and POCl$_3$ (2.64 mL, 28.45 mmol) at 90° C. and the mixture was refluxed for 4 hours. The solution was poured into ice water, and then sodium bicarbonate was added to pH 8. The reaction mixture was extracted with ethyl acetate and washed with 5% aqueous potassium bisulfate, and brine. The organic layer was dried over sodium sulfate and concentrated in vacuo. The crude was purified by silica gel column chromatography using a n-heptane to n-heptane/EtOAc, 8/2 gradient. The desired fractions were pooled and evaporated to dryness to afford 49 ethyl 2,6-dichloro-5-fluoropyrimidine-4-carboxylate.

Preparation of 50

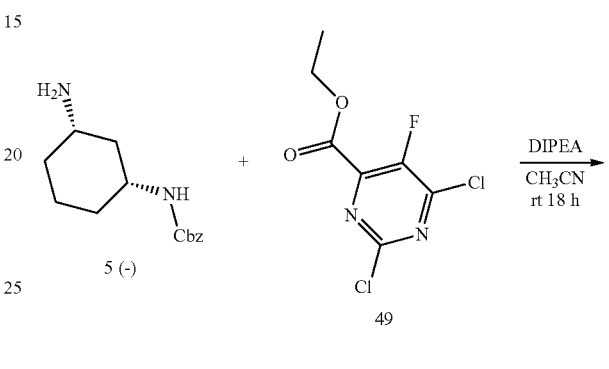

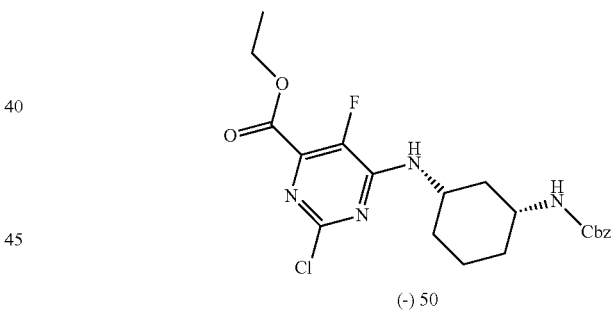

50 was prepared according to the method to prepare 34. LC-MS ES$^+$ m/z=451.2; Rt: 1.09 min, method A Preparation of 51

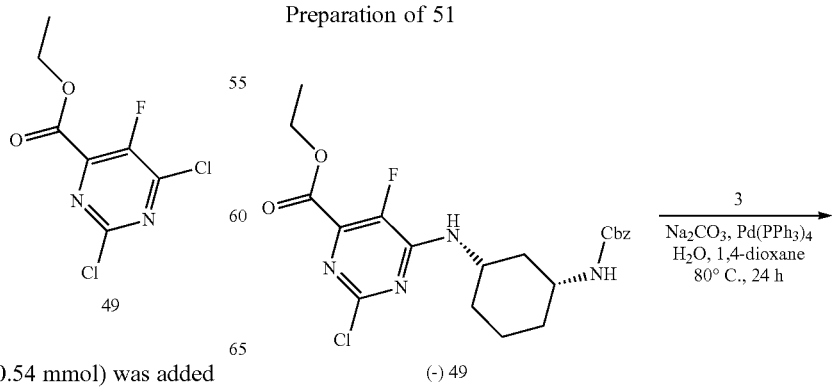

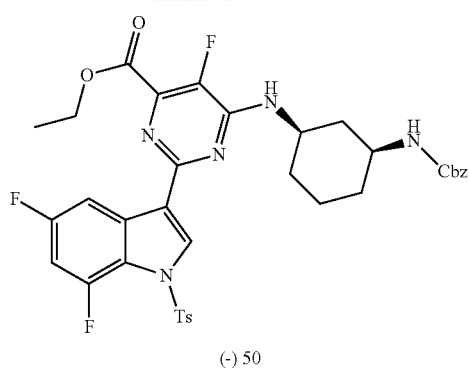

(-) 50

51 was prepared according to the method to prepare 32. LC-MS ES+ m/z=722.4; Rt: 2.56 min, method B Preparation of 52

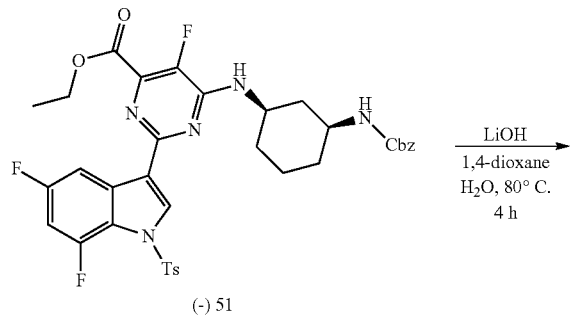

(-) 51

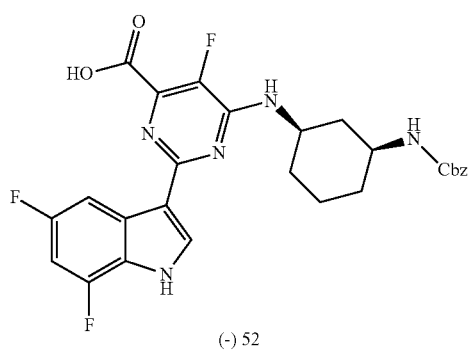

(-) 52

In a 250 mL flask 51 (1 g, 1.56 mmol) was stirred in 1,4-dioxane (45 mL) at rt, while a solution of LiOH (374 mg, 15.63 mmol) in water (5 mL) was added. The mixture was heated between 80 and 90° C. for about 4 hours. The reaction mixture was neutralized with HCl 37% and the solvent was removed under reduced pressure. The water layer was extracted with EtOAc, dried over MgSO$_4$, the solids were removed by filtration, and the solvent of the filtrate was removed under reduced pressure to afford 52. LC-MS ES+ m/z=540.2; Rt: 0.83 min, method A Preparation of 53

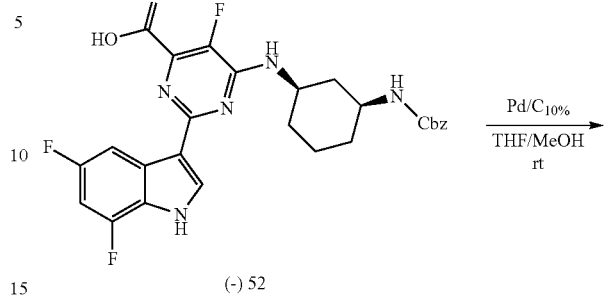

(-) 52

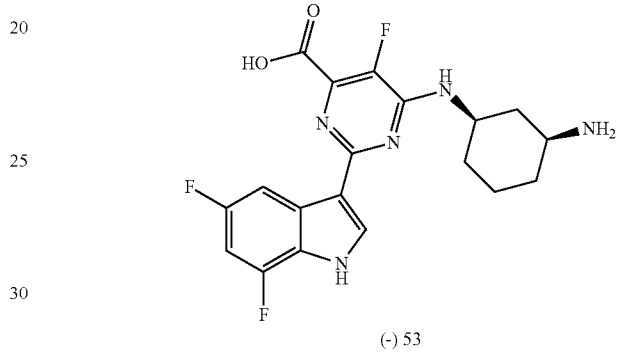

(-) 53

Pd/C (10%) (172 mg, 0.16 mmol) was added to a mixture of CH$_3$OH (15 mL) and THF (15-mL) under N$_2$. Afterwards, 52 (580 mg, 1.08 mmol) was added and the reaction mixture was stirred at room temperature under H$_2$ atmosphere until 1 eq. H$_2$ was consumed. The catalyst was removed by filtration over dicalite. The filtrate was concentrated under reduced pressure to afford 53. LC-MS ES+ m/z=406.3; Rt: 1.03 min, method B.

Preparation of 54

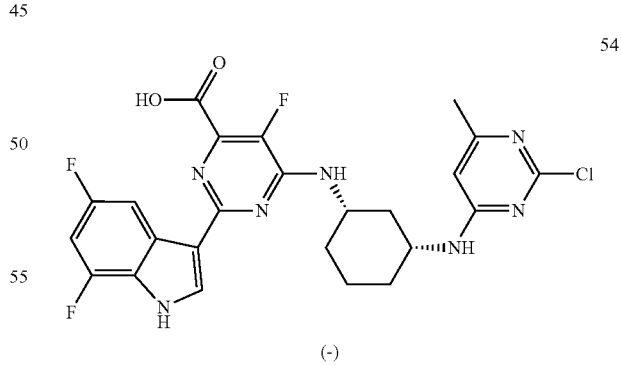

54

(-)

54 was prepared according to the method to prepare 34. $^1$H NMR (400 MHz, DMSO-d$_6$) δ ppm 1.07-1.63 (m, 4H) 1.93 (m, 3H) 2.14 (s, 3H) 2.17-2.26 (m, 1H) 3.86-4.04 (m, 1H) 4.12-4.30 (m, 1H) 6.22 (br s, 1H) 6.96-7.14 (m, 1H) 7.54-7.69 (m, 1H) 7.75 (br s, 1H) 8.06 (br d, J=11.9 Hz, 1H) 8.18 (s, 1H) 12.18 (br s, 1H) LC-MS ES+ m/z=532.1; Rt: 1.41 min, method B.

Preparation of 55

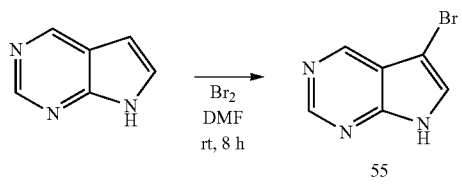 [SMILES: c1ncc2cc[nH]c2n1 ; Brc1c[nH]c2ncncc12]

To a stirred solution of 7H-pyrrolo[2,3-d]pyrimidine (11.5 g, 73.92 mmol) in DMF (350 mL) was added a solution of bromine (11.8 g, 73.84 mmol) in DMF (50 mL) at 0° C. The cooling bath was removed and the reaction was stirred at 20° C. for 8 h, then the reaction mixture was poured into ice-water and basified with $Na_2CO_3$. The mixture was extracted with ethyl acetate. The combined organic layers were washed with 10% aq. $Na_2S_2O_3$ solution, brine, dried over $MgSO_4$, the solids were removed by filtration, and the filtrate was concentrated under reduced pressure to afford 55, 5-bromo-7H-pyrrolo[2,3-d]pyrimidine as yellow solid, used in the next step without further purification. $^1$H NMR (400 MHz, DMSO-$d_6$) δ ppm 7.84 (s, 1H), 8.84 (s, 1H), 8.92 (s, 1H), 12.57 (br, 1H).

Preparation of 56

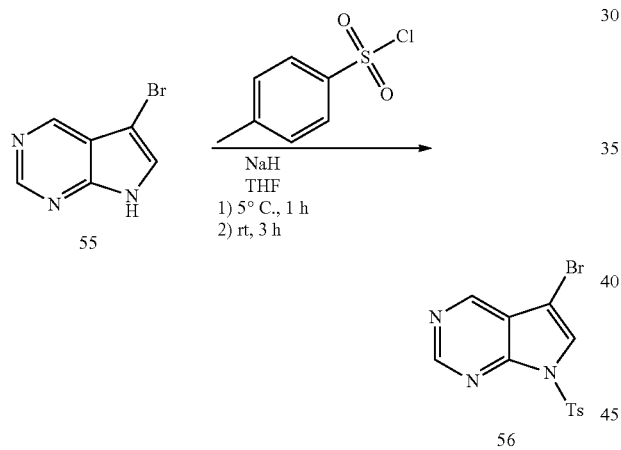

To a stirred solution of 5-bromo-7H-pyrrolo[2,3-d]pyrimidine (12.8 g, 55.11 mmol) in THF was added NaH (4.48 g, 112.01 mmol) portion wise at 0° C. under nitrogen. The mixture was stirred at 5° C. for 1 hour then p-toluenesulfonyl chloride (11.6 g, 60.85 mmol) was added portion wise. The reaction mixture was allowed to warm to 20° C. and stirred for 3 hours. The reaction mixture was poured into a mixture of ice and 1M aq. HCl while stirring. The mixture was extracted with ethyl acetate. The combined organic layers were washed with brine, dried over $MgSO_4$, the solids were removed by filtration and the filtrate was concentrated under reduced pressure. The crude was purified by crystallization from ethyl acetate to afford 56, 5-bromo-7-tosyl-7H-pyrrolo[2,3-d]pyrimidine as white solid. $^1$H NMR (400 MHz, DMSO-$d_6$) δ ppm 2.36 (s, 3H), 7.47 (d, J=8.0 Hz, 2H), 8.06 (d, J=8.0 Hz, 2H), 8.31 (s, 1H), 9.03 (s, 1H), 9.06 (s, 1H). LC-MS ES$^+$ m/z=351.8; Rt: 2.02 min, method D.

Preparation of 57

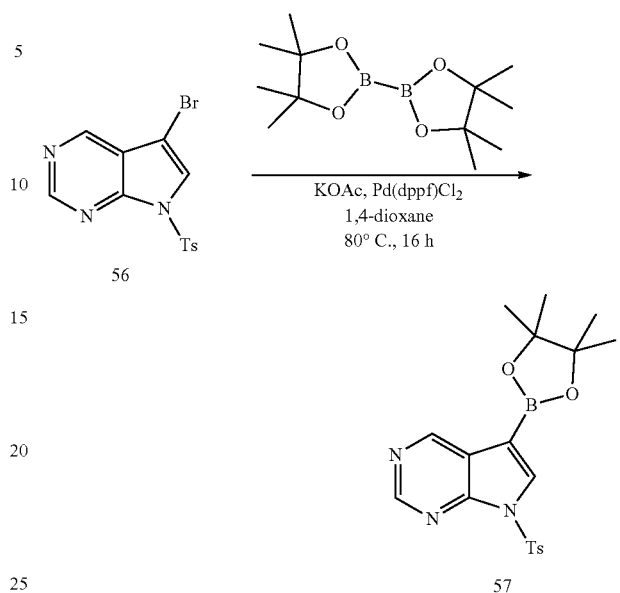

A mixture of 5-bromo-7-tosyl-7H-pyrrolo[2,3-d]pyrimidine (10 g, 28.39 mmol), bis(pinacolato)diboron (14.42 g, 56.79 mmol), potassium acetate (8.36 g, 85.18 mmol), Pd(dppf)Cl$_2$ (1 g, 1.37 mmol) in 1,4-dioxane (170 mL, degassed with nitrogen) was heated at 80° C. for 16 hours under nitrogen in a 500 mL round bottom flask equipped with a reflux condenser. The reaction mixture was cooled to room temperature, filtered through packed Celite and the solid was rinsed with ethyl acetate. The filtrate was concentrated under reduced pressure and the crude was purified by silica column chromatography using a n-heptane to ethyl acetate gradient. The desired fractions were collected and concentrated under reduced pressure to afford 57, 5-(4,4,5,5-tetramethyl-1,3,2-dioxaborolan-2-yl)-7-tosyl-7H-pyrrolo[2,3-d]pyrimidine. $^1$H NMR (400 MHz, DMSO-$d_6$) δ ppm 1.33 (s, 12H) 2.37 (s, 3H) 7.47 (d, J=8.36 Hz, 2H) 8.11 (d, J=8.58 Hz, 2H) 8.14 (s, 1H) 9.00 (s, 1H) 9.10 (s, 1H). LC-MS ES$^+$ m/z=318.1; Rt: 0.74 min, method A.

Preparation of 58

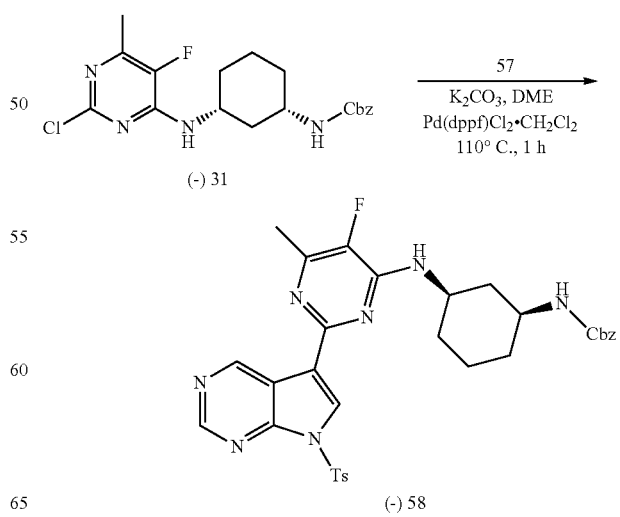

In a sealed tube, a solution of 57 (1.525 g, 3.82 mmol), 31 (1.6 g, 4.07 mmol), and K₂CO₃ (5.73 mL, 2 M, 11.46 mmol) in DME (24 mL) was purged with N₂ for 5 min and then Pd(dppf)Cl₂·CH₂Cl₂ (313 mg, 0.38 mmol) was added. The mixture was stirred and heated in an autoclave at 110° C. for 60 min, then was filtered over dicalite and the filtrate was concentrated under reduced pressure. The crude was purified via silica column chromatography using a n-heptane to 25% EtOAc in n-heptane gradient. The solvents of the best fractions were removed under reduced pressure to afford 58. LC-MS ES⁺ m/z=630.2; Rt: 1.28 min, method A Preparation of 59

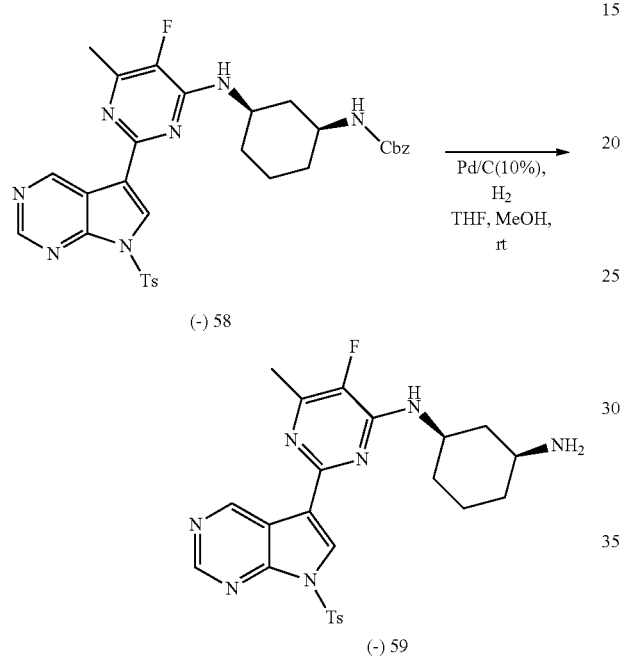

(-) 58

Pd/C(10%), H₂
THF, MeOH, rt (-) 59

Pd/C (10%) (173 mg, 0.16 mmol) was added to a mixture of CH₃OH (15 mL) and THF (15 mL) under N₂. Afterwards, 58 (410 mg, 0.65 mmol) was added and the reaction mixture was stirred at rt under H₂ atmosphere until 1 eq. of H₂ was consumed. The catalyst was removed by filtration over Dicalite. The filtrate was concentrated under reduced pressure.

The crude was dissolved in CH₂Cl₂ and treated with a mixture of 6N HCl in IPA. The formed precipitate was isolated by filtration then dried in vacuo to afford 59. LC-MS ES⁺ m/z=496.2; Rt: 0.89 min, method A.

Preparation of 60 and 61

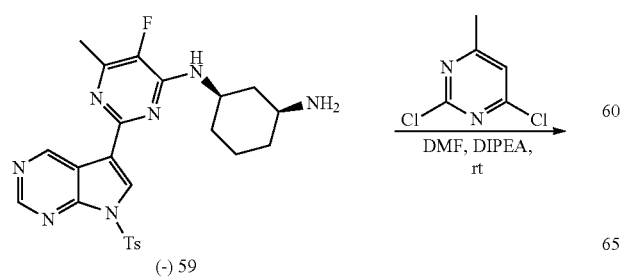

(-) 59

DMF, DIPEA, rt

-continued

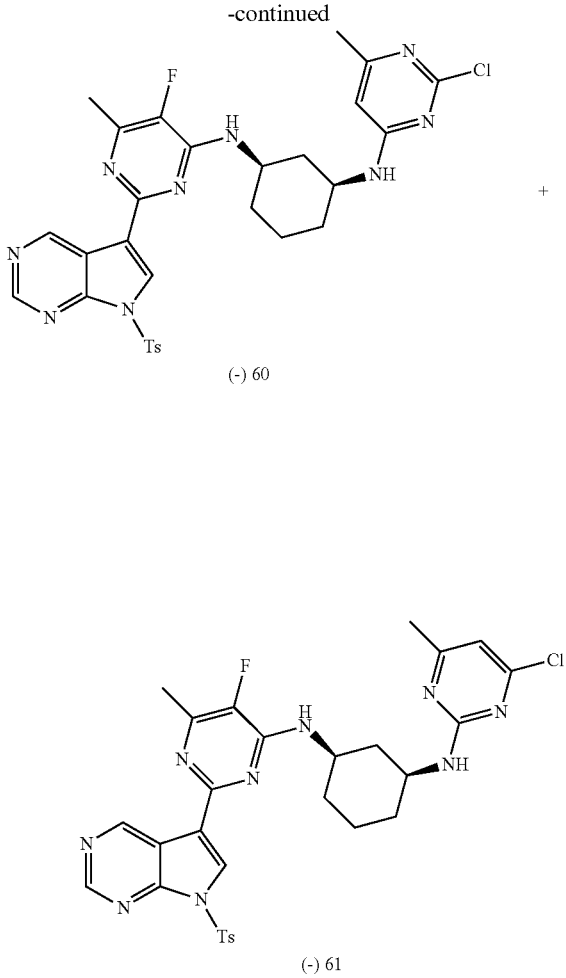

(-) 60

(-) 61

A solution of 2,4-dichloro-6-methylpyrimidine (303 mg, 1.86 mmol) and DIPEA (0.53 mL, 3.10 mmol) in DMF (15 mL) was stirred at room temperature under a nitrogen. Then 59 (330 mg, 0.62 mmol) was added and stirring continued four hours at 60° C. The mixture was poured into ice water and stirred overnight. The precipitate was collected by filtration and dried in vacuo to afford a mixture of 60 and 61.

Preparation of 62 and 63

Mixture of 60/61 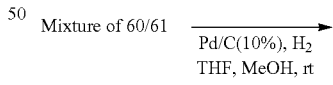
Pd/C(10%), H₂
THF, MeOH, rt

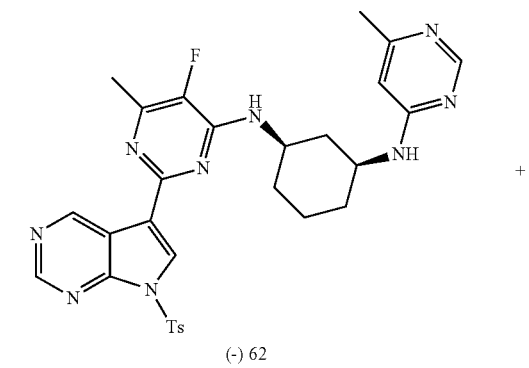

(-) 62

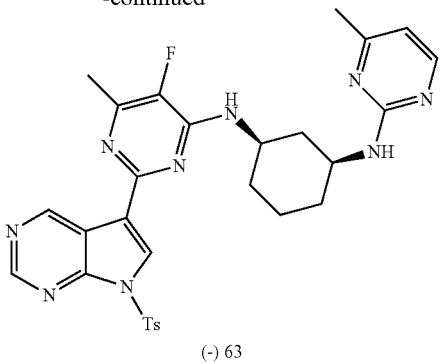

(-) 63

Pd/C (10%) (102 mg, 0.10 mmol) was added to a mixture of CH₃OH (30 mL) and THF (15 mL) under N₂ atmosphere. Afterwards, a mixture of 60 and 61 (240 mg, 0.39 mmol) was added and the reaction mixture was stirred at rt under H₂ atmosphere until 1 eq. hydrogen was consumed. The catalyst was removed by filtration over Dicalite. The filtrate was concentrated under reduced pressure to afford a mixture of 62 and 63.

Preparation of 64 and 65

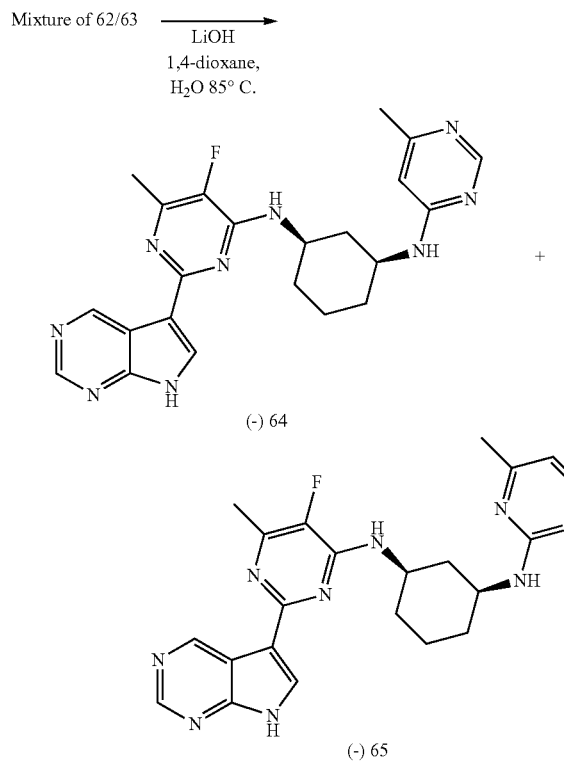

In a 100 mL flask a mixture of 62 and 63 (110 mg, 0.19 mmol) was stirred in 1,4-dioxane (18 mL) at 85° C., while a solution of LiOH (90 mg, 3.74 mmol) in water (2 mL) was added.

The mixture was brought to reflux for 1 hour and was allowed to stir overnight at ambient temperature. 1,4-dioxane was evaporated and the crude was reconstituted in ethyl acetate (20 mL), stirred and neutralized with conc. HCl. The solvent was removed under reduced pressure. The crude was purified via preparatory HPLC (stationary phase: RP XBridge Prep C18 ODB 5 μm, 30×250 mm, mobile phase: 0.25% NH₄HCO₃ solution in water, CH₃CN). The desired fractions were collected and evaporated to dryness to afford 64. ¹H NMR (400 MHz, DMSO-d₆) δ ppm 1.10-1.45 (m, 3H) 1.50-1.59 (m, 1H) 1.81-1.92 (m, 1H) 1.93-2.07 (m, 2H) 2.16 (s, 3H) 2.29-2.37 (m, 1H) 2.33 (d, J=3.2 Hz, 3H) 3.84-4.03 (m, 1H) 4.07-4.31 (m, 1H) 6.33 (s, 1H) 7.00 (br d, J=7.3 Hz, 1H) 7.12-7.33 (m, 1H) 8.09 (s, 1H) 8.29 (s, 1H) 8.78 (s, 1H) 9.66 (s, 1H) 12.19 (br s, 1H). LC-MS ES⁺ m/z=434.3; Rt: 0.72 min, method A. And 65 ¹H NMR (400 MHz, DMSO-d₆) δ ppm 1.15-1.43 (m, 3H) 1.43-1.57 (m, 1H) 1.81-1.88 (m, 1H) 1.90-2.01 (m, 2H) 2.17 (s, 3H) 2.27 (m, 1H) 2.33 (d, J=2.9 Hz, 3H) 3.84-4.00 (m, 1H) 4.08-4.22 (m, 1H) 6.39 (d, J=5.0 Hz, 1H) 7.00 (br d, J=7.7 Hz, 1H) 7.36 (m, 1H) 8.08 (d, J=5.0 Hz, 1H) 8.14 (s, 1H) 8.80 (s, 1H) 9.66 (s, 1H). LC-MS ES⁺ m/z=434.3; Rt: 1.64 min, method B.

Preparation of 66

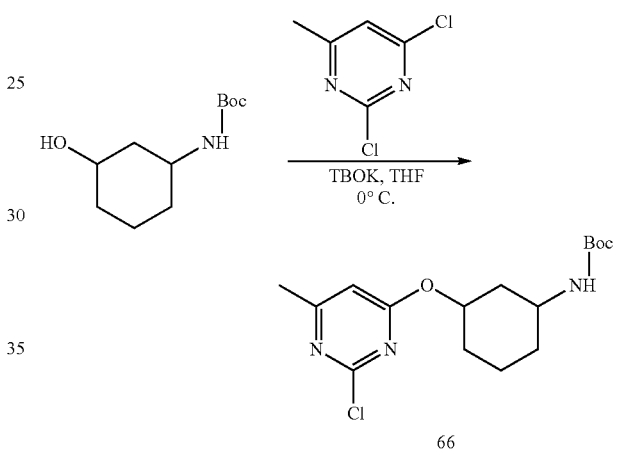

66

To a mixture of t-butyl (3-hydroxycyclohexyl) carbamate (3.0 g, 16.5 mmol) in dry THF (20 mL) in properly dried and inert condition, 2,4-dichloro-6-methylpyrimidine (2.781 g, 16.72 mmol) was added drop wise under nitrogen atmosphere. The reaction mixture was stirred for 15-20 min at room temperature followed by addition of potassium t-butoxide drop wise at 0° C. After 1 h, the reaction was quenched with cold water at 0° C. and aqueous was extracted with EtOAc and washed with brine. The organic phase was dried and concentrated to get crude material. The crude was purified via silica column chromatography using a n-heptane to EtOAc gradient. The solvents of the best fractions were removed under reduced pressure to afford 66. LC-MS ES⁺ m/z=342.2; Rt: 2.14 min, method C Preparation of 67

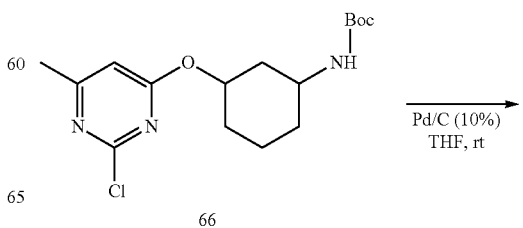

66

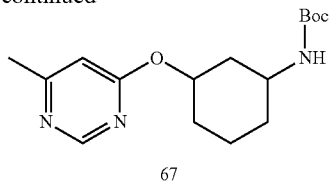

67

Pd/C (10%) (934 mg, 0.88 mmol) was added to a mixture of THF (80 mL) under N$_2$. Afterwards, 66 (3 g, 8.78 mmol) was added and the reaction mixture was stirred at room temperature under H$_2$ until 1 eq. hydrogen was consumed. The catalyst was removed by filtration over Dicalite. The filtrate was concentrated under reduced pressure to afford a mixture of 67. LC-MS ES$^+$ m/z=308.2; Rt: 0.96 min, method A Preparation of 68

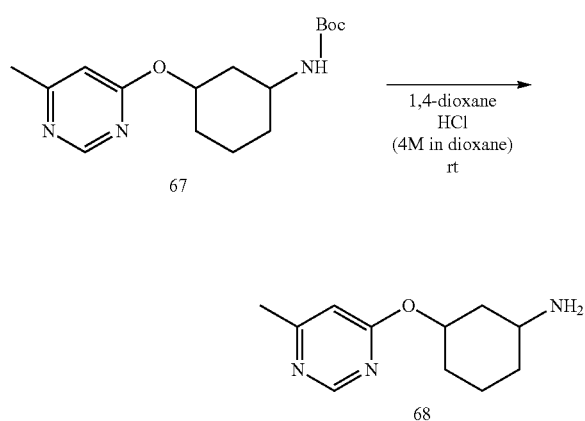

Into a 100 mL round bottom flask equipped with a magnetic stir bar, was added 67 (3 g, 9.76 mmol) in 1,4-dioxane (25 mL). 4M HCL in 1,4-dioxane (12 mL) was added slowly while stirring at room temperature for 18 hours. The solvent was removed under reduced pressure and crude 68 was used in the next step.

Preparation of 69

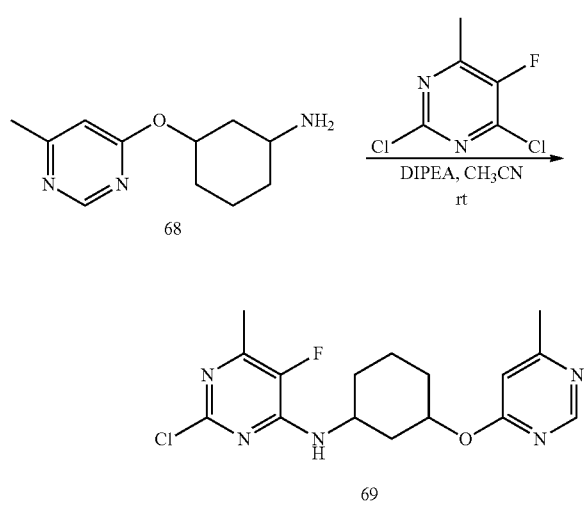

A solution of 2,4-dichloro-5-fluoro-6-methylpyrimidine (0.78 g, 4.31 mmol) and DIPEA (1.77 mL, 10.26 mmol) in CH$_3$CN (20 mL) was stirred at rt under N$_2$. Then 68 (1 g, 4.10 mmol) was added and stirring was continued for 16 hours at room temperature. The reaction mixture was concentrated under reduced pressure and the crude was purified by silica column chromatography using a n-heptane to ethyl acetate gradient. The desired fractions were collected and concentrated under reduced pressure to afford 69

Preparation of 70

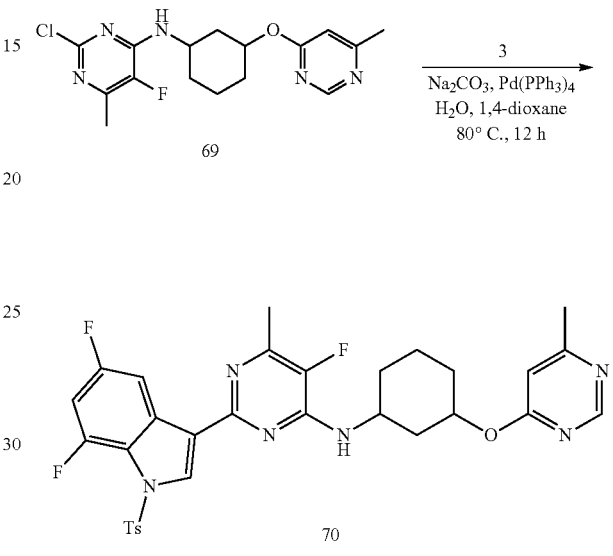

70 was prepared according to the method to prepare 7. LC-MS ES$^+$ m/z=623.2; Rt: 2.73 min, method D.

Preparation of 71

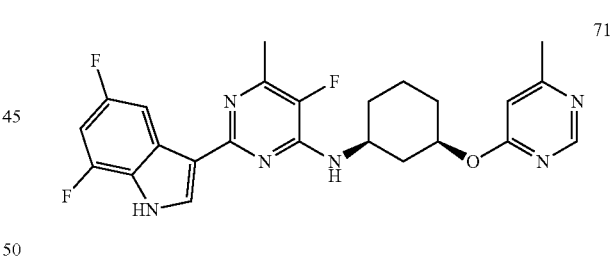

71 was prepared according to the method to prepare 64. A purification was performed via preparatory SFC (stationary phase: Chiralpak Diacel AD-H 20 mm×250 mm, mobile phase: CO$_2$, isopropanol+0.4% isopropylamine) to afford 71. $^1$H NMR (600 MHz, DMSO-d$_6$) δ ppm 1.33-1.42 (m, 1H) 1.34-1.42 (m, 1H) 1.51-1.59 (m, 2H) 1.89 (m, 1H) 2.03 (m, 1H) 2.15 (m, 1H) 2.27 (m, 1H) 2.32 (d, J=2.8 Hz, 3H) 2.46-2.53 (m, 1H) 4.20 (m, 1H) 5.20 (m, 1H) 6.76 (s, 1H) 7.04 (m, 1H) 7.34 (d, 1H) 8.06 (m, 1H) 8.14 (s, 1H) 8.59 (s, 1H) 12.18 (br s, 1H). LC-MS ES$^+$ m/z=469.2; Rt: 2.30 min, method D. Analytical SFC-MS Rt: 3.79 min, m/z=469.1. (Analytical SFC Conditions: stationary phase: Chiralpak Diacel AD-H 4.6 mm×250 mm, mobile phase A:CO$_2$, B: EtOH+0.2% isopropylamine, gradient: 25% B hold 4 min, then to 50% B in 1 min, hold for 2 min. The flow rate was 5 mL/min and column temperature was 40° C.).

TABLE 1

Compounds of formula (I) and corresponding analytical data. Compounds were prepared according to the methods described above or analogous methods thereof.

| Cmpnd # | STRUCTURE | ¹H NMR | LC Rt (min) | LC Method | LC-MS Mass Found [M + H]⁺ | MP °C. |
|---|---|---|---|---|---|---|
| 11 | 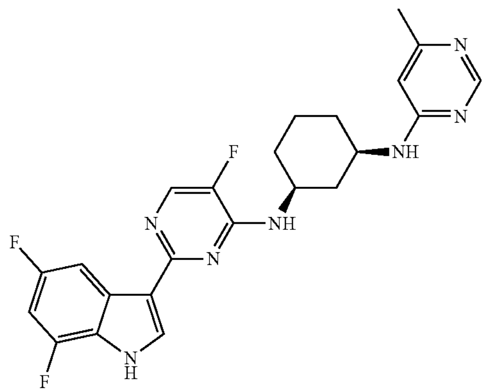 [SMILES: Cc1cc(N[C@@H]2CCC[C@H](Nc3nc(-c4c[nH]c5c(F)cc(F)cc45)ncc3F)C2)ncn1] | ¹H NMR (400 MHz, DMSO-$d_6$) δ ppm 1.17-1.59 (m, 3H) 1.83-2.35 (m, 5H) 3.17 (s, 3H) 4.06-4.22 (m, 2H) 6.28 (s, 1H) 7.05 (m, 1H) 7.20 (d, J = 7.92 Hz, 1H) 7.50 (m, 1H) 8.04 (m, 1H) 8.14 (d, J = 3.96 Hz, 1H) 8.16 (s, 1H) 8.25 (s, 1H) 11.02-13.04 (m, 1H) | 1.86 | B | 453.0 | |
| 12 | 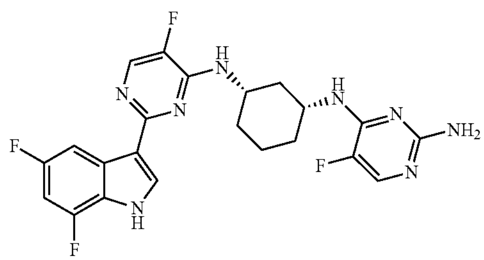 [SMILES: Nc1ncc(F)c(N[C@@H]2CCC[C@H](Nc3nc(-c4c[nH]c5c(F)cc(F)cc45)ncc3F)C2)n1] | ¹H NMR (400 MHz, DMSO-$d_6$) δ ppm 1.21-1.42 (m, 2H) 1.53 (m, 2H) 1.83-1.96 (m, 2H) 2.06-2.24 (m, 2H) 4.00-4.17 (m, 2H) 5.75 (s, 2H) 6.99-7.09 (m, 2H) 7.54 (m, 1H) 7.61 (m, 1H) 7.99-8.04 (m, 1H) 8.11 (s, 1H) 8.14 (d, J = 3.96 Hz, 1H) 12.16 (br s, 1H) | 1.88 | B | 473.1 | |
| 13 | 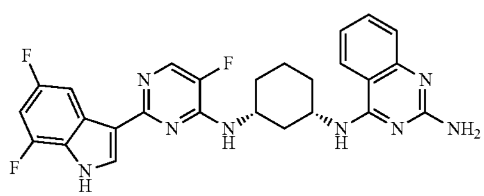 [SMILES: Nc1nc(N[C@H]2CCC[C@@H](Nc3nc(-c4c[nH]c5c(F)cc(F)cc45)ncc3F)C2)c2ccccc2n1] | | 1.80 | D | 505.5 | |
| 14 | 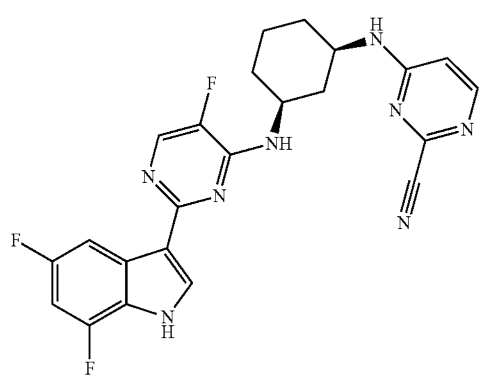 [SMILES: N#Cc1nccc(N[C@@H]2CCC[C@H](Nc3nc(-c4c[nH]c5c(F)cc(F)cc45)ncc3F)C2)n1] | ¹H NMR (300 MHz, chloroform-d) δ ppm 1.21-1.42 (m, 4H) 1.62-1.76 (m, 1H) 1.99-2.26 (m, 3H) 2.86 (m, 1H) 4.01-4.34 (m, 2H) 4.86 (m, 1H) 6.44 (m, 1H) 6.72-6.85 (m, 1H) 8.03-8.05 (m, 1H) 8.03-8.11 (m, 1H) 8.13-8.20 (m, 1H) 8.89 (m, 1H) | 2.79 | C | 464.9 | 215.6 |

TABLE 1-continued

Compounds of formula (I) and corresponding analytical data. Compounds were prepared according to the methods described above or analogous methods thereof.

| Cmpnd # | STRUCTURE | ¹H NMR | Rt (min) | LC Method | LC-MS Mass Found [M + H]⁺ | MP °C. |
|---|---|---|---|---|---|---|
| 15 | 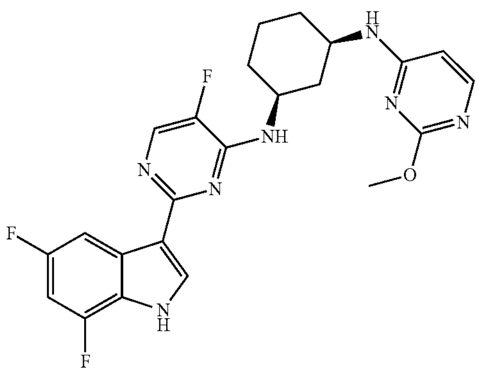 [SMILES: COc1nccc(N[C@@H]2CCC[C@H](Nc3nc(-c4c[nH]c5c(F)cc(F)cc45)ncc3F)C2)n1] | ¹H NMR (300 MHz, methanol-d₄) δ ppm 1.10-1.51 (m, 5H) 1.64-1.74 (m, 1H) 1.94-2.02 (m, 1H) 2.16 (s, 1H) 2.46-2.52 (m, 1H) 3.79 (s, 3H) 3.95-4.14 (m, 1H) 4.37 (m, 1H) 5.99 (m, 1H) 6.75-6.86 (m, 1H) 7.90 (m, 1H) 7.97 (m, 1H) 8.03-8.09 (m, 2H) | 2.25 | C | 469.2 | 139.6 |
| 16 | 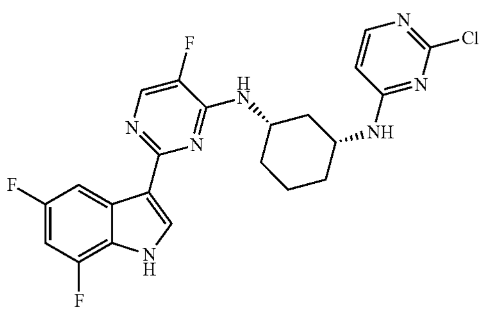 [SMILES: Fc1cc(F)c2[nH]cc(-c3ncc(F)c(N[C@H]4CCC[C@@H](Nc5ccnc(Cl)n5)C4)n3)c2c1] | ¹H NMR (360 MHz, DMSO-d₆) δ ppm 1.01-1.05 (m, 1H) 1.14-1.38 (m, 2H) 1.40-1.60 (m, 2H) 1.86 (m, 1H) 1.94-2.10 (m, 2H) 2.20-2.32 (m, 1H) 3.89-4.02 (m, 1H) 4.14-4.25 (m, 1H) 6.40 (m, 1H) 7.02-7.10 (m, 1H) 7.54 (m, 1H) 7.88 (m, 1H) 7.94 (m, 1H) 8.02 (m, 1H) 8.14-8.16 (m, 1H) 12.19 (br s, 1H) | 1.26 | B | 473.4 | |
| 18 | 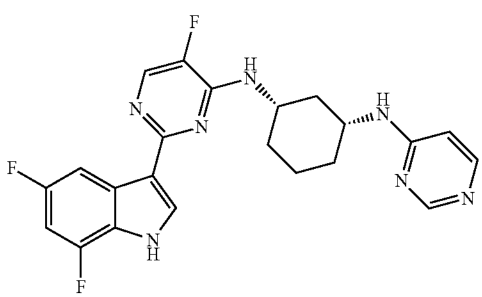 [SMILES: Fc1cc(F)c2[nH]cc(-c3ncc(F)c(N[C@H]4CCC[C@@H](Nc5ccncn5)C4)n3)c2c1] | ¹H NMR (300 MHz, methanol-d₄) δ ppm 1.23-1.55 (m, 3H) 1.59-1.82 (m, 1H) 1.89-2.64 (m, 4H) 3.96-4.19 (m, 1H) 4.26-4.39 (m, 1H) 6.47 (m, 1H) 6.76-6.86 (m, 1H) 7.89-8.00 (m, 2H) 8.04-8.11 (m, 2H) 8.31 (s, 1H) | 1.98 | C | 440.1 | 166.5 |
| 19 | 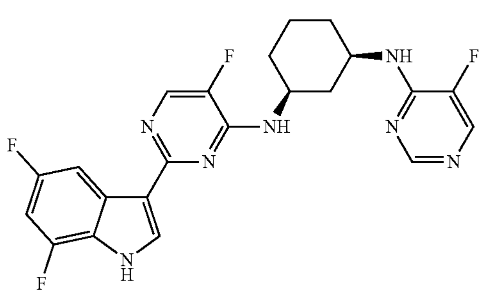 [SMILES: Fc1cc(F)c2[nH]cc(-c3ncc(F)c(N[C@H]4CCC[C@@H](Nc5ncncc5F)C4)n3)c2c1] | ¹H NMR (300 MHz, methanol-d₄) δ ppm 1.36-1.81 (m, 4H) 1.93-2.62 (m, 4H) 4.30 (m, 2H) 6.80 (m, 1H) 7.96 (s, 1H) 7.91-8.01 (m, 1H) 8.08 (s, 1H) 8.03-8.12 (m, 1H) 8.16 (br s, 1H) | 2.25 | C | 457.9 | 215.6 |

TABLE 1-continued

Compounds of formula (I) and corresponding analytical data. Compounds were prepared according to the methods described above or analogous methods thereof.

| Cmpnd # | STRUCTURE | ¹H NMR | Rt (min) | LC Method | LC-MS Mass Found [M + H]⁺ | MP °C. |
|---|---|---|---|---|---|---|
| 20 | 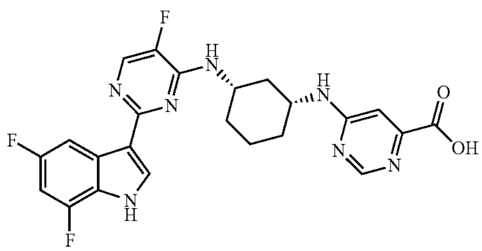 [SMILES: O=C(O)c1cc(N[C@@H]2CCC[C@H](Nc3nc(-c4c[nH]c5c(F)cc(F)cc45)ncc3F)C2)ncn1] | ¹H NMR (300 MHz, methanol-d₄) δ ppm 1.24-1.73 (m, 4H) 1.90-2.52 (m, 4H) 3.97-4.21 (m, 1H) 4.23-4.45 (m, 1H) 6.66-6.93 (m, 1H) 7.04 (s, 1H) 7.99 (d, J = 4.1 Hz, 1H) 8.04 (m, 1H) 8.08 (s, 1H) 8.21 (s, 1H) | 2.10 | C | 483.9 | |
| 36 | 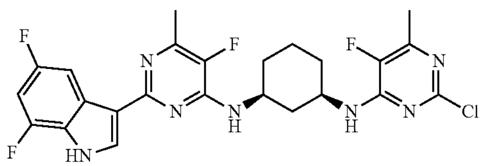 [SMILES: Cc1nc(Cl)nc(N[C@@H]2CCC[C@H](Nc3nc(-c4c[nH]c5c(F)cc(F)cc45)nc(C)c3F)C2)c1F] | ¹H NMR (400 MHz, DMSO-d₆) δ ppm 1.26-1.41 (m, 2H) 1.46-1.61 (m, 2H) 1.82-1.94 (m, 2H) 1.98-2.06 (m, 1H) 2.15-2.18 (m, 1H) 2.21 (d, J = 2.9 Hz, 3H), 2.32 (d, J = 2.9 Hz, 3H) 4.02 (m, 1H) 4.16 (m, 1H) 7.02 (m, 1H) 7.32 (m, 1H) 7.92 (m, 1H) 8.04 (d, J = 9.9 Hz, 1H) 8.11 (s, 1H) 12.11 (br s, 1H) | 1.21 | A | 520.2 | |
| 37 | 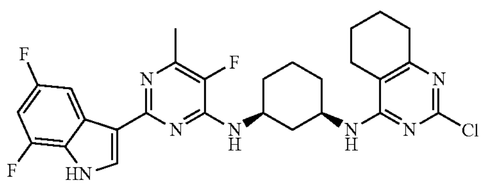 [SMILES: Cc1nc(-c2c[nH]c3c(F)cc(F)cc23)nc(N[C@H]2CCC[C@@H](Nc3nc(Cl)nc4c3CCCC4)C2)c1F] | ¹H NMR (400 MHz, DMSO-d₆) δ ppm −0.01-0.01 (m, 1H) 1.25-1.42 (m, 2H) 1.47-1.60 (m, 2H) 1.67-1.77 (m, 4H) 1.83-1.98 (m, 2H) 2.03-2.11 (m, 1H) 2.23-2.31 (m, 3H) 2.32 (d, J = 2.9 Hz, 3H) 2.50-2.53 (m, 2H) 4.05-4.20 (m, 2H) 6.41 (m, 1H) 6.85 (m, 1H) 6.91 (m, 1H) 8.04 (s, 1H) 8.02-8.06 (m, 1H) 11.78 (br s, 1H) | 2.34 | C | 542.2 | |
| 38 | 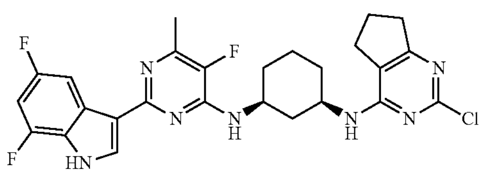 [SMILES: Cc1nc(-c2c[nH]c3c(F)cc(F)cc23)nc(N[C@H]2CCC[C@@H](Nc3nc(Cl)nc4c3CCC4)C2)c1F] | ¹H NMR (400 MHz, DMSO-d₆) δ ppm 1.24-1.37 (m, 2H) 1.46-1.59 (m, 2H) 1.82-2.07 (m, 5H) 2.18 (m, J = 11.7 Hz, 1H) 2.32 (d, J = 2.9 Hz, 3H) 2.61 (m, 2H) 2.69 (t, J = 7.7 Hz, 2H) 4.01-4.11 (m, 1H) 4.11-4.21 (m, 1H) 7.03 (m, 1H) 7.19 (m, 1H) 7.30 (m, 1H) 8.05 (d, J = 9.9 Hz, 1H) 8.11 (s, 1H) 12.11 (br s, 1H) | 2.25 | C | 528.2 | |
| 39 | 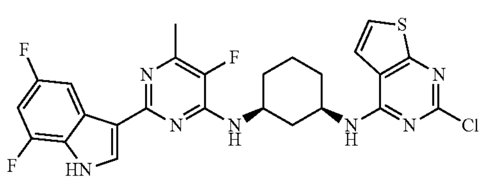 [SMILES: Cc1nc(-c2c[nH]c3c(F)cc(F)cc23)nc(N[C@H]2CCC[C@@H](Nc3nc(Cl)nc4sccc34)C2)c1F] | ¹H NMR (400 MHz, DMSO-d₆) δ ppm 1.29-1.43 (m, 2H) 1.50-1.65 (m, 2H) 1.86-1.97 (m, 1H) 2.00-2.12 (m, 2H) 2.28 (m, 1H) 2.33 (d, J = 2.9 Hz, 3H) 4.14-4.29 (m, 2H) 7.03 (m, 1H) 7.36 (br s, 1H) 7.57 (m, 1H) 7.68 (d, J = 5.9 Hz, 1H) 8.06 (m, 1H) 8.13 (d, J = 2.9 Hz, 1H) 8.24 (m, 1H) 12.13 (br s, 1H) | 1.25 | A | 544.2 | |
| 40 | 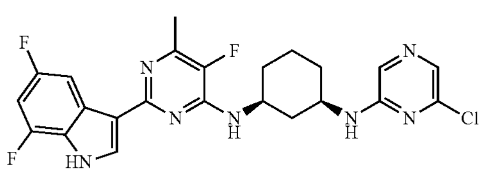 [SMILES: Cc1nc(-c2c[nH]c3c(F)cc(F)cc23)nc(N[C@H]2CCC[C@@H](Nc3cncc(Cl)n3)C2)c1F] | ¹H NMR (400 MHz, DMSO-d₆) δ ppm 1.20-1.29 (m, 1H) 1.35-1.42 (m, 1H) 1.42-1.53 (m, 1H) 1.54-1.65 (m, 1H) 1.88-1.96 (m, 1H) 2.05-2.14 (m, 2H) 2.30-2.36 (m, 1H) 2.38 (d, J = 2.9 Hz, 3H) 3.83-3.92 (m, 1H) 4.19-4.28 (m, 1H) 7.06-7.12 (m, 1H) 7.38 (m, 1H) 7.64 (m, 1H) 7.71 (s, 1H) 7.91 (s, 1H) 8.11 (m, 1H) 8.18 (s, 1H) 12.2 (br s, 1H) | 3.37 | B | 488.1 | 201.8 |
| 41 | 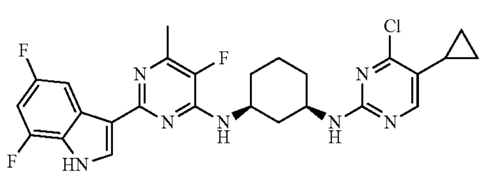 [SMILES: Cc1nc(-c2c[nH]c3c(F)cc(F)cc23)nc(N[C@H]2CCC[C@@H](Nc3ncc(C4CC4)c(Cl)n3)C2)c1F] | ¹H NMR (400 MHz, DMSO-d₆) δ ppm 0.55-0.62 (m, 2H) 0.81-0.87 (m, 2H) 1.16-1.54 (m, 4H) 1.69-1.77 (m, 1H) 1.78-1.87 (m, 1H) 1.90-2.04 (m, 2H) 2.20-2.26 (m, 1H) 2.30 (d, J = 2.9 Hz, 3H) 3.76-3.88 (m, 1H) 4.06-4.18 (m, 1H) 6.97-7.07 (m, 1H) 7.25-7.32 (m, 1H) 7.49 (m, 1H) 7.98 (s, 1H) 8.01-8.07 (m, 1H) 8.10 (s, 1H) 12.12 (br s, 1H) | 3.70 | B | 528.2 | 222.7 |

TABLE 1-continued

Compounds of formula (I) and corresponding analytical data. Compounds were prepared according to the methods described above or analogous methods thereof.

| Cmpnd # | STRUCTURE | ¹H NMR | Rt (min) | LC Method | LC-MS Mass Found [M + H]⁺ | MP ° C. |
|---|---|---|---|---|---|---|
| 42 | 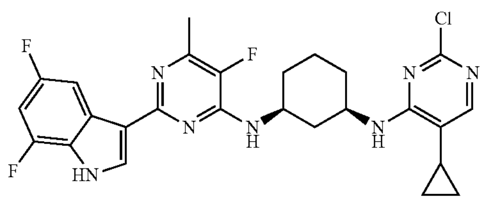 [SMILES: Cc1nc(-c2c[nH]c3c(F)cc(F)cc23)nc(N[C@H]2CCC[C@@H](Nc3nc(Cl)ncc3C3CC3)C2)c1F] | ¹H NMR (400 MHz, DMSO-d₆) δ ppm 0.50-0.60 (m, 2H) 0.84-0.91 (m, 2H) 1.26-1.65 (m, 5H) 1.83-1.98 (m, 2H) 2.02-2.09 (m, 1H) 2.17-2.25 (m, 1H) 2.32 (d, J = 2.9 Hz, 3H) 4.09-4.22 (m, 2H) 6.97-7.10 (m, 2H) 7.32 (d, 1H) 7.67 (s, 1H) 8.05 (m, 1H) 8.11 (d, 1H) 12.1 (m, 1H) | 3.43 | B | 528.2 | |
| 43 | 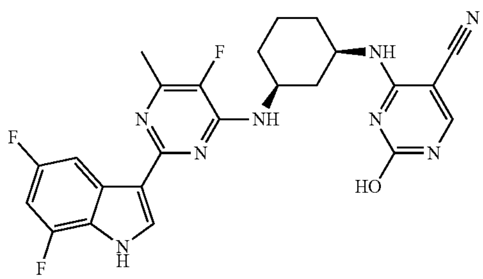 [SMILES: Cc1nc(-c2c[nH]c3c(F)cc(F)cc23)nc(N[C@H]2CCC[C@@H](Nc3nc(O)ncc3C#N)C2)c1F] | ¹H NMR (400 MHz, DMSO-d₆,) δ ppm 1.23-1.40 (m, 2H) 1.44-1.58 (m, 2H) 1.84-1.91 (m, 1H) 2.00 (m, 1H) 2.07 (m, 1H) 2.32 (d, J = 2.9 Hz, 3H) 2.31-2.38 (m, 1H) 3.95-4.04 (m, 1H) 4.09-4.18 (m, 1H) 6.95-7.03 (m, 2H) 7.36 (br s, 1H) 8.05 (m, 1H) 8.08 (d, 1H) 8.19 (s, 1H) 11.07 (br s, 1H) 11.93 (br s, 1H) | 2.76 | B | 495.1 | |
| 44 | 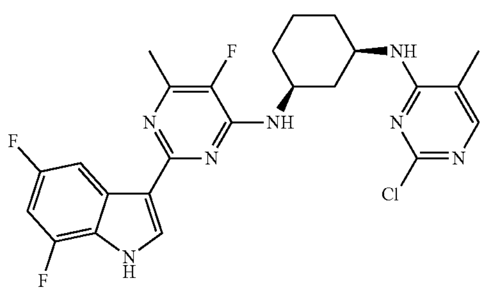 [SMILES: Cc1cnc(Cl)nc1N[C@@H]1CCC[C@H](Nc2nc(-c3c[nH]c4c(F)cc(F)cc34)nc(C)c2F)C1] | ¹H NMR (400 MHz, DMSO-d₆) δ ppm 1.28-1.42 (m, 2H) 1.49-1.61 (m, 2H) 1.83-1.89 (m, 1H) 1.93 (d, J = 11.7 Hz, 1H) 1.97 (s, 3H) 2.05 (m, 1H) 2.19 (m, 1H) 2.32 (d, J = 2.9 Hz, 3H) 4.08-4.21 (m, 2H) 7.00-7.07 (m, 2H) 7.35 (m, 1H) 7.78 (s, 1H) 8.05 (m, 1H) 8.12 (d, J = 2.5 Hz, 1H) 12.14 (m, 1H) | 3.18 | B | 502.1 | 185.4 |
| 45 | 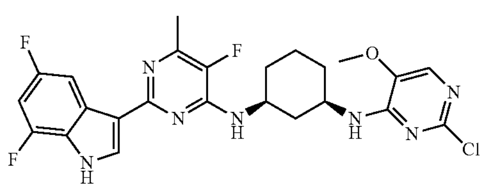 [SMILES: COc1cnc(Cl)nc1N[C@@H]1CCC[C@H](Nc2nc(-c3c[nH]c4c(F)cc(F)cc34)nc(C)c2F)C1] | ¹H NMR (400 MHz, DMSO-d₆) δ ppm 1.26-1.35 (m, 1H) 1.35-1.46 (m, 1H) 1.48-1.63 (m, 2H) 1.81-1.91 (m, 2H) 2.03 (m, 1H) 2.15 (m, 1H) 2.32 (d, J = 2.9 Hz, 3H) 3.83 (s, 3H) 4.00-4.10 (m, 1H) 4.10-4.20 (m, 1H) 7.01-7.07 (m, 1H) 7.35 (m, 1H) 7.42 (m, 1H) 7.65 (s, 1H) 8.05 (m, 1H) 8.11 (d, J = 2.1 Hz, 1H) 12.14 (br s, 1H) | 3.18 | B | 518.1 | 246.6 |
| 46 | 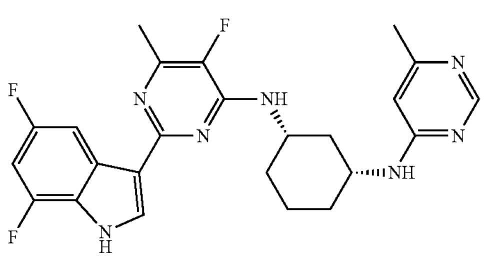 [SMILES: Cc1cc(N[C@@H]2CCC[C@H](Nc3nc(-c4c[nH]c5c(F)cc(F)cc45)nc(C)c3F)C2)ncn1] | ¹H NMR (400 MHz, DMSO-d₆) δ ppm −0.01-0.01 (m, 1H) 1.14-1.39 (m, 3H) 1.46-1.59 (m, 1H) 1.82-1.90 (m, 1H) 1.94-2.08 (m, 2H) 2.13 (s, 3H) 2.27-2.30 (m, 1H) 2.32 (d, J = 2.9 Hz, 3H) 3.84-4.04 (m, 1H) 4.12-4.19 (m, 1H) 6.27 (s, 1H) 7.01-7.08 (m, 1H) 7.19 (m, 1H) 7.29 (m, 1H) 7.95 (s, 1H) 8.06 (m, 1H) 8.12 (s, 1H) 8.25 (s, 1H) 12.15 (s, 1H) | 1.00 | A | 468.3 | |
| 47 | 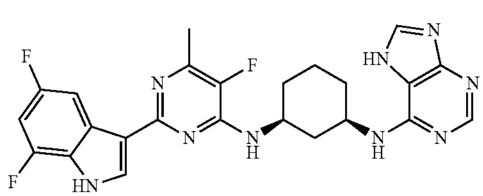 [SMILES: Cc1nc(-c2c[nH]c3c(F)cc(F)cc23)nc(N[C@H]2CCC[C@@H](Nc3ncnc4nc[nH]c34)C2)c1F] | ¹H NMR (400 MHz, DMSO-d₆) δ ppm 1.29-1.62 (m, 4H) 1.84-1.92 (m, 1H) 1.94-2.11 (m, 2H) 2.30-2.34 (m, 1H) 2.31 (d, J = 2.9 Hz, 3H) 4.09-4.22 (m, 1H) 4.23-4.44 (m, 1H) 6.95-7.10 (m, 1H) 7.31 (m, 1H) 7.51 (m, 1H) 8.01 (m, 1H) 7.93-8.10 (m, 1H) 8.12 (s, 1H) 8.16 (br s, 1H) 12.17 (br s, 1H) | 1.80 | C | 494.3 | |

TABLE 1-continued

Compounds of formula (I) and corresponding analytical data. Compounds were prepared according to the methods described above or analogous methods thereof.

| Cmpnd # | STRUCTURE | ¹H NMR | Rt (min) | LC Method | LC-MS Mass Found [M + H]⁺ | MP ° C. |
|---|---|---|---|---|---|---|
| 54 | 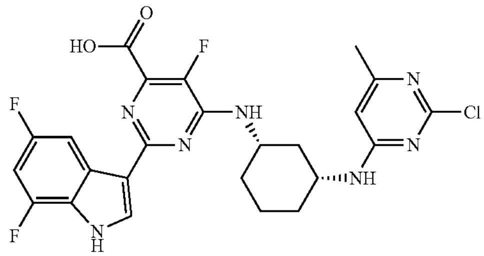 [SMILES: Cc1cc(N[C@@H]2CCC[C@H](Nc3nc(-c4c[nH]c5c(F)cc(F)cc45)nc(C(=O)O)c3F)C2)nc(Cl)n1] | ¹H NMR (400 MHz, DMSO-d₆) δ ppm 1.07-1.63 (m, 4H) 1.93 (m, 3H) 2.14 (s, 3H) 2.17-2.26 (m, 1H) 3.86-4.04 (m, 1H) 4.12-4.30 (m, 1H) 6.22 (br s, 1H) 6.96-7.14 (m, 1H) 7.54-7.69 (m, 1H) 7.75 (br s, 1H) 8.06 (m, 1H) 8.18 (s, 1H) 12.18 (br s, 1H) | 1.41 | B | 532.1 | |
| 64 | 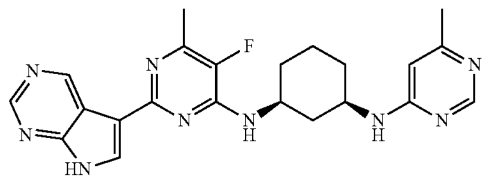 [SMILES: Cc1cc(N[C@@H]2CCC[C@H](Nc3nc(-c4c[nH]c5ncncc45)nc(C)c3F)C2)ncn1] | ¹H NMR (400 MHz, DMSO-d₆) δ ppm 1.10-1.45 (m, 3H) 1.50-1.59 (m, 1H) 1.81-1.92 (m, 1H) 1.93-2.07 (m, 2H) 2.16 (s, 3H) 2.29-2.37 (m, 1H) 2.33 (d, J = 2.9 Hz, 3H) 3.84-4.03 (m, 1H) 4.07-4.31 (m, 1H) 6.33 (s, 1H) 7.00 (m, 1H) 7.12-7.33 (m, 1H) 8.09 (s, 1H) 8.29 (s, 1H) 8.78 (s, 1H) 9.66 (s, 1H) 12.19 (br s, 1H) | 0.72 | A | 434.3 | |
| 65 | 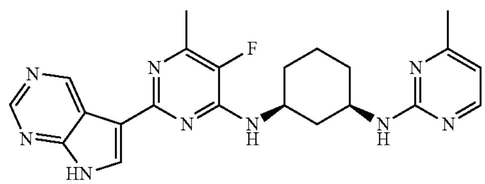 [SMILES: Cc1ccnc(N[C@@H]2CCC[C@H](Nc3nc(-c4c[nH]c5ncncc45)nc(C)c3F)C2)n1] | ¹H NMR (400 MHz, DMSO-d₆) δ ppm 1.15-1.43 (m, 3H) 1.43-1.57 (m, 1H) 1.81-1.88 (m, 1H) 1.90-2.01 (m, 2H) 2.17 (s, 3H) 2.27 (m, 1H) 2.33 (d, J = 2.9 Hz, 3H) 3.84-4.00 (m, 1H) 4.08-4.22 (m, 1H) 6.39 (m, 1H) 7.00 (m, 1H) 7.36 (m, 1H) 8.08 (d, J = 5.0 Hz, 1H) 8.14 (s, 1H) 8.80 (s, 1H) 9.66 (s, 1H) | 1.64 | B | 434.2 | |

Rt = retention time in minutes.

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the mass spectrometer (MS) which was configured with an atmospheric pressure ion source. It is within the knowledge of the skilled person to set the tune parameters (e.g. scanning range, dwell time, etc.) in order to obtain ions allowing the identification of the compound's nominal monoisotopic molecular weight (MW). Data acquisition was performed with appropriate software.

Compounds are described by their experimental retention times ($R_1$) and ions. If not specified differently in the table of data, the reported molecular ion corresponds to the [M+H]⁺ (protonated molecule) and/or [M−H]⁻ (deprotonated molecule). In case the compound was not directly ionizable the type of adduct is specified (i.e. [M+NH₄]⁺, [M+HCOO]⁻, etc.). For molecules with multiple isotopic patterns (Br, Cl, etc), the reported value is the one obtained for the lowest isotope mass. All results were obtained with experimental uncertainties that are commonly associated with the method used.

| Method code | Instrument | Column | Mobile phase | Gradient | Flow Column T (° C.) | Run time (min) |
|---|---|---|---|---|---|---|
| A | Waters: Acquity ® UPLC ® -DAD and SQD | Waters: BEH C18 (1.7 μm, 2.1 × 50 mm) | A: 10 mM CH₃COONH₄ in 95% H₂O + 5% CH₃CN B: CH₃CN | From 95% A to 5% A in 1.3 min, held for 0.7 min. | 0.8 55 | 2 |
| B | Waters: Acquity UPLC ® - DAD and Quattro Micro ™ | Waters: BEH C18 (1.7 μm, 2.1 × 100 mm) | A: 95% CH₃COONH₄ 7 mM/5% CH₃CN, B: CH₃CN | 84.2% A for 0.49 min, to 10.5% A in 2.18 min, held for 1.94 min, back to 84.2% AB in 0.73 min, held for 0.73 min. | 0.343 40 | 6.2 |
| C | Waters: Acquity ® UPLC ® -DAD and SQD | Waters: HSS T3 (1.8 μm, 2.1 × 100 mm) | A: 10 mM CH₃COONH₄ in 95% H₂O + | From 100% A to 5% A in 2.10 min, | 0.7 55 | 3.5 |

| Method code | Instrument | Column | Mobile phase | Gradient | Flow Column T (° C.) | Run time (min) |
|---|---|---|---|---|---|---|
| D | Waters: Acquity ® UPLC ® - DAD and SQD | Waters: HSS T3 (1.8 µm, 2.1 × 100 mm) | A: 10 mM $CH_3COONH_4$ in 95% H2O + 5% $CH_3CN$ B: $CH_3CN$ | From 100% A to 5% A in 2.10 min, to 0% A in 0.90 min, to 5% A in 0.5 min | 0.8 55 | 3.5 |

"SQD" Single Quadrupole Detector, "RT" room temperature, "BEH" bridged ethylsiloxane/silica hybrid, "HSS" High Strength Silica, "DAD" Diode Array Detector. Flow expressed in mL/min; column temperature (T) in ° C.; Run time in minutes.

Biological Activity of Compounds of Formula (I)

The in vitro antiviral activity of the compounds was determined using a cell-based antiviral assay. In this assay, the cytopathic effect (CPE) in Madin-Darby canine kidney (MDCK) cells infected by influenza virus A/Taiwan/1/86 (H1N1) was monitored in the presence or absence of the compounds. White 384-well microtiter assay plates (Greiner) were filled via acoustic drop ejection using the echo liquid handler (Labcyte, Sunnyvale, Calif.). Two hundred nanoliter of compound stock solutions (100% DMSO) were transferred to the assay plates. MDCK cells were dispensed to the plate at final density of 25,000 or 6,000 cells/well. Then Influenza A/Taiwan/1/86 (H1N1) virus was added at a multiplicity of infection of 0.001 or 0.01, respectively. The wells contain 0.5% DMSO per volume. Virus- and mock-infected controls were included in each test. The plates were incubated at 37° C. in 5% $CO_2$. Three days post-virus exposure, the cytopathic effect was quantified by measuring the reduction in ATP levels using the ATPlite™ kit (PerkinElmer, Zaventem, Belgium) according to the manufacturer's instructions. The $IC_{50}$ was defined as the 50% inhibitory concentration. In parallel, compounds were incubated for three days in white 384-well microtiter plates and the in vitro cytotoxicity of compounds in MDCK cells was determined by measuring the ATP content of the cells using the ATPlite™ kit (PerkinElmer, Zaventem, Belgium) according to the manufacturer's instructions. Cytotoxicity was reported as $CC_{50}$, the concentration that causes a 50% reduction in cell viability.

TABLE 2

Biological Activity of compounds of formula (I).

| Compound # | Influenza A/Taiwan/1/86 $IC_{50}$ µM | TOX MDCK $CC_{50}$ µM |
|---|---|---|
| 10 | 0.02 | 2.88 |
| 11 | 0.008 | 5.97 |
| 12 | 0.006 | >1 |
| 13 | 0.02 | 11.55 |
| 14 | 0.008 | 3.15 |
| 15 | 0.075 | 3.19 |
| 16 | 0.008 | 2.17 |
| 17 | 0.009 | 5.57 |
| 18 | 0.008 | 8.34 |
| 19 | 0.14 | >25 |
| 29 | 0.008 | 3.05 |
| 35 | 0.03 | 0.89 |
| 36 | 0.002 | >25 |
| 37 | 0.011 | >25 |

TABLE 2-continued

Biological Activity of compounds of formula (I).

| Compound # | Influenza A/Taiwan/1/86 $IC_{50}$ µM | TOX MDCK $CC_{50}$ µM |
|---|---|---|
| 38 | 0.001 | >25 |
| 39 | 0.003 | >25 |
| 40 | 0.024 | >25 |
| 41 | 0.039 | >25 |
| 42 | 0.041 | >25 |
| 43 | 0.0006 | >25 |
| 44 | 0.01 | >25 |
| 45 | 0.036 | >25 |
| 46 | 0.002 | >25 |
| 47 | 0.0007 | 11 |
| 54 | 0.061 | >25 |
| 64 | 0.008 | >25 |
| 65 | 0.007 | >25 |
| 71 | 0.013 | 2.2 |

The invention claimed is:

1. A compound having the structural formula

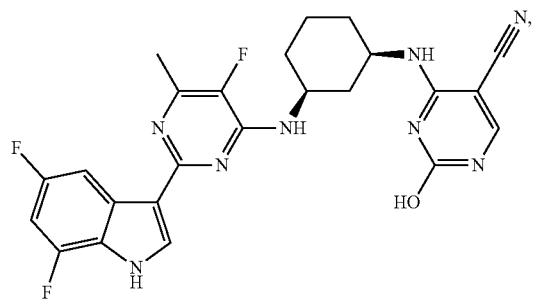 [SMILES: Cc1nc(-c2c[nH]c3c(F)cc(F)cc23)nc(N[C@H]2CCC[C@@H](Nc3nc(O)ncc3C#N)C2)c1F]

a stereo-isomeric form, a pharmaceutically acceptable salt, solvate or polymorph thereof.

2. A pharmaceutical composition comprising the compound according to claim 1, stereo-isomeric form, pharmaceutically acceptable salt, solvate or polymorph thereof, and one or more pharmaceutically acceptable excipients, diluents or carriers.

3. A method of treating viral influenza infection in a patient, said method comprising administering to the patient in need thereof an effective amount of a compound having the structural formula

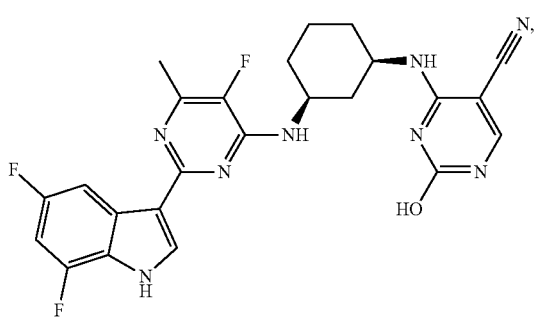 [SMILES: Cc1nc(-c2c[nH]c3c(F)cc(F)cc23)nc(N[C@H]2CCC[C@@H](Nc3nc(O)ncc3C#N)C2)c1F]

a stereo-isomeric form, a pharmaceutically acceptable salt, solvate or polymorph thereof.

4. The method of claim 3, wherein the compound, stereoisomeric form, pharmaceutically acceptable salt, solvate or polymorph thereof, is administered as a pharmaceutical composition comprising one or more pharmaceutically acceptable excipients, diluents, or carriers.

5. The method of claim 3, further comprising co-administering to said patient an additional therapeutic agent.

6. The method of claim 5, wherein the additional therapeutic agent is selected from an antiviral agent or influenza vaccine, or both.

7. The method of claim 6, wherein the additional therapeutic agent is an antiviral agent.

8. A method of inhibiting replication of influenza virus(es) in a biological sample, said method comprising administering to the biological sample a compound having the structural formula

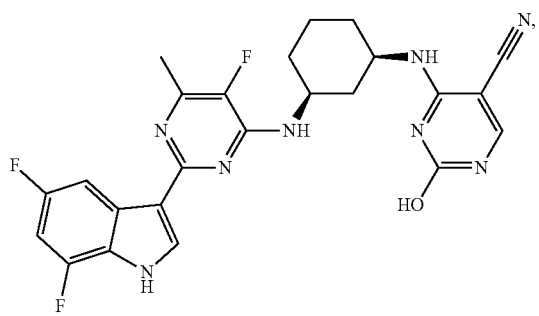 [SMILES: Cc1nc(-c2c[nH]c3c(F)cc(F)cc23)nc(N[C@H]2CCC[C@@H](Nc3nc(O)ncc3C#N)C2)c1F]

a stereo-isomeric form, a pharmaceutically acceptable salt, solvate or polymorph thereof.

* * * * *